(12) United States Patent
Ishihara

(10) Patent No.: US 8,489,179 B2
(45) Date of Patent: *Jul. 16, 2013

(54) FLUOROSCOPY APPARATUS, FLUOROSCOPY SYSTEM AND FLUORESCENCE-IMAGE PROCESSING METHOD

(75) Inventor: Yasushige Ishihara, Tokyo (JP)

(73) Assignee: Olympus Corporation, Tokyo (JP)

( * ) Notice: Subject to any disclaimer, the term of this patent is extended or adjusted under 35 U.S.C. 154(b) by 37 days.

This patent is subject to a terminal disclaimer.

(21) Appl. No.: 13/221,031

(22) Filed: Aug. 30, 2011

(65) Prior Publication Data

US 2011/0313297 A1 Dec. 22, 2011

Related U.S. Application Data

(63) Continuation of application No. PCT/JP2010/054426, filed on Mar. 16, 2010.

(30) Foreign Application Priority Data

Mar. 24, 2009 (JP) ................................. 2009-072849

(51) Int. Cl.
*A61B 6/00* (2006.01)

(52) U.S. Cl.
USPC ........... 600/476; 600/407; 600/477; 382/128; 382/154

(58) Field of Classification Search
USPC ............ 600/476, 477, 478; 250/458.1, 559.3; 382/154
See application file for complete search history.

(56) References Cited

U.S. PATENT DOCUMENTS

| 7,309,867 | B2 * | 12/2007 | Costa et al. ................ 250/458.1 |
| 7,679,785 | B2 * | 3/2010 | Ehbets et al. .................. 358/1.9 |
| 7,873,407 | B2 * | 1/2011 | Levenson et al. ............. 600/476 |
| 8,193,517 | B2 * | 6/2012 | Ishihara ..................... 250/458.1 |
| 2005/0153356 | A1 * | 7/2005 | Okawa et al. ..................... 435/6 |
| 2011/0176723 | A1 * | 7/2011 | Ali et al. ....................... 382/154 |

FOREIGN PATENT DOCUMENTS

| JP | 62-247232 | A | 10/1987 |
| JP | 03-58729 | B | 9/1991 |
| JP | 2001-137173 | A | 5/2001 |
| JP | 2003-036436 | A | 2/2003 |
| JP | 2006-175052 | A | 7/2006 |

OTHER PUBLICATIONS

International Search Report dated May 11, 2010 from corresponding Japanese Patent Application No. PCT/JP2010/054426.

* cited by examiner

*Primary Examiner* — Baisakhi Roy
(74) *Attorney, Agent, or Firm* — Scully, Scott, Murphy & Presser, P.C.

(57) ABSTRACT

Provided is a fluoroscopy apparatus (1) including an illumination portion (4) provided with a light source (3) that radiates illumination light and excitation light; a fluorescence imaging unit (18) that acquires a fluorescence image by imaging fluorescence generated at an subject (X); a return-light imaging unit (17) that acquires a reference image by imaging return light returning from the subject (X); and an image-correcting unit (6) that corrects the fluorescence image imaged by the fluorescence imaging unit (18) by using the reference image imaged by the return-light imaging unit (17), wherein the image-correcting unit (6) performs the following processing:

$$FL_{revised} = A \times FL_{before}^{x} / B \times RL_{before}^{y},$$

where $FL_{revised}$ is a luminance value of a corrected fluorescence image, $FL_{before}$ and $RL_{before}$ are luminance values of acquired fluorescence image and reference image, A and B are constants, and x and y are exponents for staying within a permissible error.

11 Claims, 13 Drawing Sheets

FLUOROSCOPY APPARATUS, FLUOROSCOPY SYSTEM AND FLUORESCENCE-IMAGE PROCESSING METHOD

CROSS-REFERENCE TO RELATED APPLICATIONS

This is a continuation of International Application PCT/JP2010/054426, with an international filing date of Mar. 16, 2010, which is hereby incorporated by reference herein in its entirety. This application claims the benefit of Japanese Patent Application No. 2009-072849, the content of which is incorporated herein by reference.

TECHNICAL FIELD

The present invention relates to a fluoroscopy apparatus, a fluoroscopy system, and a fluorescence-image processing method.

BACKGROUND ART

With a known method in the related art (for example, see Patent Literatures 1 to 3), brightness variation in a fluorescence image due to observation distance and observation angle is corrected by dividing a fluorescence image by a reflected-light image.

CITATION LIST

Patent Literature

{PTL 1} Japanese Unexamined Patent Application, Publication No. Sho 62-247232.
{PTL 2} Japanese Examined Patent Application, Publication No. Hei 3-58729.
{PTL 3} Japanese Unexamined Patent Application, Publication No. 2006-175052.

SUMMARY OF INVENTION

Technical Problem

Fluorescence and reflected light differ in terms of the dependency of the acquired brightness on observation distance and the dependency thereof on observation angle; therefore, the influences of distance and angle cannot be completely corrected by simply dividing a fluorescence image by a reflected-light image.

The present invention provides a fluoroscopy apparatus, a fluoroscopy system, and a fluorescence-image processing method that enable observation with a fluorescence image having high quantitativeness by satisfactorily removing dependencies on distance and angle remaining in an image that has been subjected to division.

Solution to Problem

A fluoroscopy apparatus according to a first aspect of the present invention is a fluoroscopy apparatus including an illumination portion provided with a light source that radiates illumination light and excitation light; a fluorescence imaging unit that acquires a fluorescence image by imaging fluorescence generated at an subject; a return-light imaging unit that acquires a reference image by imaging return light returning from the subject; and an image-correcting unit that corrects the fluorescence image acquired by the fluorescence imaging unit by using the reference image imaged by the return-light imaging unit, wherein the image-correcting unit performs the following processing:

$$FL_{revised} = FL_{after}/RL_{after},$$

where, $FL_{revised}$ is a luminance value of the corrected fluorescence image, $FL_{after} = A \times FL_{before}^{x}$,
$RL_{after} = B \times RL_{before}^{y}$, $FL_{before}$ and $RL_{before}$ are luminance values of the acquired fluorescence image and reference image, A and B are constants, $$x = (cn-dm)/(bc-ad) \quad (1),$$

$$y = (an-bm)/(bc-ad) \quad (2),$$

a is an exponent obtained by applying a power approximation to a characteristic of luminance versus distance from the illumination portion to the subject, for the fluorescence image obtained by the fluorescence imaging unit when excitation light of a predetermined intensity is radiated toward the subject, b is an exponent obtained by applying a power approximation to a characteristic of luminance versus cosine from the illumination portion to the subject, for the fluorescence image obtained by the fluorescence imaging unit when excitation light of a predetermined intensity is radiated toward the subject, c is an exponent obtained by applying a power approximation to a characteristic of luminance versus distance from the illumination portion to the subject, for the reference image obtained by the return-light imaging unit when illumination light of a predetermined intensity is radiated toward the subject, d is an exponent obtained by applying a power approximation to a characteristic of luminance versus cosine from the illumination portion to the subject, for the reference image obtained by the return-light imaging unit when illumination light of a predetermined intensity is radiated toward the subject, $$r_D^{|m|} \cdot r_\theta^{|n|} \leq 1 + e_{max} \quad (3),$$

$r_D = D_{max}/D_{min}$,
$r_\theta = \cos\theta_{min}/\cos\theta_{max}$,
$D_{max}$ is a presumed maximum observation distance,
$D_{min}$ is a presumed minimum observation distance,
$\theta_{max}$ is a presumed maximum observation angle,
$\theta_{min}$ is a presumed minimum observation angle (where, $0° \leq \theta_{min} < \theta_{max} \leq 90°$),
m and n are arbitrary constants that satisfy Expression (3)
$e_{max}$ is $(FL_{after}/RL_{after})_{max} \div (FL_{after}/RL_{after})_{min} - 1$,
$(FL_{after}/RL_{after})_{max}$ is a maximum value within a range from the presumed minimum observation distance to the presumed maximum observation distance and within a range from the presumed minimum observation angle to the presumed maximum observation angle,
$(FL_{after}/RL_{after})_{min}$ is a minimum value within a range from the presumed minimum observation distance to the presumed maximum observation distance and within a range from the presumed minimum observation angle to the presumed maximum observation angle, and
when bc−ad=0, x and y are set from arbitrary real numbers that satisfy x:y=c:a=d:b.

A fluoroscopy apparatus according to a second aspect of the present invention is a fluoroscopy apparatus including an illumination portion provided with a light source that radiates illumination light and excitation light; a fluorescence imaging unit that acquires a fluorescence image by imaging fluorescence generated at a subject; a return-light imaging unit that acquires a reference image by imaging return light returning from the subject; and an image-correcting unit that corrects the fluorescence image acquired by the fluorescence imaging unit by using the reference image imaged by the return-light imaging unit, wherein the image-correcting unit performs the following processing:

$$FL_{revised} = FL_{after}/RL_{after})^{1/x},$$

where $FL_{revised}$ is a luminance value of the corrected fluorescence image, $FL_{after} = A \times FL_{before}^{x}$,
$RL_{after} = B \times RL_{before}^{y}$, $FL_{before}$ and $RL_{before}$ are luminance values of the acquired fluorescence image and reference image, A and B are constants, $$x:y = c:(a-m) = d:(b-n) \quad (4),$$

a is an exponent obtained by applying a power approximation to a characteristic of luminance versus distance from the illumination portion to the subject, for the fluorescence image obtained by the fluorescence imaging unit when excitation light of a predetermined intensity is radiated toward the subject, b is an exponent obtained by applying a power approximation to a characteristic of luminance versus cosine from the illumination portion to the subject, for the fluorescence image obtained by the fluorescence imaging unit when excitation light of a predetermined intensity is radiated toward the subject, c is an exponent obtained by applying a power approximation to a characteristic of luminance versus distance from the illumination portion to the subject, for the reference image obtained by the return-light imaging unit when illumination light of a predetermined intensity is radiated toward the subject, d is an exponent obtained by applying a power approximation to a characteristic of luminance versus cosine from the illumination portion to the subject, for the reference image obtained by the return-light imaging unit when illumination light of a predetermined intensity is radiated toward the subject, $$r_D^{|m|} \cdot r_\theta^{|n|} \leq 1 + e_{max} \quad (3),$$

$r_D = D_{max}/D_{min}$,
$r_\theta = \cos\theta_{min}/\cos\theta_{max}$,
$D_{max}$ is a presumed maximum observation distance,
$D_{min}$ is a presumed minimum observation distance,
$\theta_{max}$ is a presumed maximum observation angle,
$\theta_{min}$ is a presumed minimum observation angle (where, $0° \leq \theta_{min} < e_{max} \leq 90°$), m and n are arbitrary constants that satisfy Expression (4) and Expression (3), $e_{max}$ is $(FL_{after}/RL_{after})_{max} \div (FL_{after}/RL_{after})_{min} - 1$, $(FL_{after}/RL_{after})_{max}$ is a maximum value within a range from the presumed minimum observation distance to the presumed maximum observation distance and within a range from the presumed minimum observation angle to the presumed maximum observation angle, and $(FL_{after}/RL_{after})_{min}$ is a minimum value within a range from the presumed minimum observation distance to the presumed maximum observation distance and within a range from the presumed minimum observation angle to the presumed maximum observation angle.

In the first aspect and the second aspect described above, m=0 may be set.

In the first aspect described above, the image-correcting unit may additionally raise the luminance value $FL_{revised}$ of the corrected fluorescence image to the $1/x^{th}$ power.

In the first aspect described above, an attachable/detachable part that is detached/attached to change observation conditions may be provided; the attachable/detachable part may store identification information; and an identification-information reading device that reads the identification information stored in the attachable/detachable part and a storage unit that stores the identification information in association with the exponents x and y may be provided.

In the second aspect described above, the illumination portion may emit illumination light of a predetermined wavelength; the exponents x and y may be set so as to substantially satisfy x:y=c:a or x:y=d:b; and the wavelength of the illumination light may be set so that an absolute value of $\epsilon$ becomes a minimum value assuming that ad−bc=$\epsilon$.

A fluoroscopy system according to a third aspect of the present invention is a fluoroscopy system including any one of above-described fluoroscopy apparatus and a calibration device for calibrating the fluoroscopy apparatus, wherein the calibration device may be provided with a standard specimen and an observation-state setting mechanism that changeably sets an observation distance and an observation angle of the fluoroscopy apparatus relative to the standard specimen, and one of the fluoroscopy apparatus and the calibration device may be provided with an exponent calculating unit that calculates the above-described exponents a to d on the basis of the observation distance and the observation angle set with the observation-state setting mechanism and the fluorescence image and the reference image acquired by imaging the standard specimen.

A fluorescence-image processing method according to a fourth aspect of the present invention is a fluorescence-image processing method for performing the following correction processing on a fluorescence image acquired by irradiating a subject with excitation light from an illumination portion and by imaging fluorescence generated at the subject by using a reference image acquired by imaging return light returning from the subject when the subject is irradiated with illumination light from the illumination portion:

$$FL_{revised} = FL_{after}/RL_{after},$$

where, $FL_{revised}$ is a luminance value of the corrected fluorescence image, $FL_{after} = A \times FL_{before}^{x}$,
$RL_{after} = B \times RL_{before}^{y}$, $FL_{before}$ and $RL_{before}$ are luminance values of the acquired fluorescence image and reference image, A and B are constants, $$x = (cn-dm)/(bc-ad) \quad (1),$$

$$y = (an-bm)/(bc-ad) \quad (2),$$

a is an exponent obtained by applying a power approximation to a characteristic of luminance versus distance from the illumination portion to the subject, for the fluorescence image obtained when excitation light of a predetermined intensity is radiated toward the subject, b is an exponent obtained by applying a power approximation to a characteristic of luminance versus cosine from the illumination portion to the subject, for the fluorescence image obtained when excitation light of a predetermined intensity is radiated toward the subject, c is an exponent obtained by applying a power approximation to a characteristic of luminance versus distance from the illumination portion to the subject, for the reference image obtained when illumination light of a predetermined intensity is radiated toward the subject, d is an exponent obtained by applying a power approximation to a characteristic of luminance versus cosine from the illumination portion to the subject, for the reference image obtained when illumination light of a predetermined intensity is radiated toward the subject, $$r_D^{|m|} \cdot r_\theta^{|n|} \leq 1 + e_{max} \qquad (3),$$

$r_D = D_{max}/D_{min}$,
$r_\theta = \cos\theta_{min}/\cos\theta_{max}$,
$D_{max}$ is a presumed maximum observation distance,
$D_{min}$ is a presumed minimum observation distance,
$\theta_{max}$ is a presumed maximum observation angle,
$\theta_{min}$ is a presumed minimum observation angle (where, $0° \leq \theta_{min} < \theta_{max} \leq 90°$),
m and n are arbitrary constants that satisfy Expression (1),
$e_{max}$ is $(FL_{after}/RL_{after})_{max} \div (FL_{after}/RL_{after})_{min} - 1$,
$(FL_{after}/RL_{after})_{max}$ is a maximum value within a range from the presumed minimum observation distance to the presumed maximum observation distance and within a range from the presumed minimum observation angle to the presumed maximum observation angle,
$(FL_{after}/RL_{after})_{min}$ is a minimum value within a range from the presumed minimum observation distance to the presumed maximum observation distance and within a range from the presumed minimum observation angle to the presumed maximum observation angle, and when bc−ad=0, x and y are set from arbitrary real numbers that satisfy x:y=c:a=d:b.

A fluorescence-image processing method according to a fifth aspect of the present invention is a fluorescence-image processing method for performing the following correction processing on a fluorescence image acquired by irradiating a subject with excitation light from an illumination portion and by imaging fluorescence generated at the subject by using a reference image acquired by imaging return light returning from the subject when the subject is irradiated with illumination light from the illumination portion:

$$FL_{revised} = FL_{after}/RL_{after})^{1/x},$$

where, $FL_{revised}$ is a luminance value of the corrected fluorescence image,
$FL_{after} = A \times FL_{before}^{x}$,
$RL_{after} = B \times RL_{before}^{y}$,
$FL_{before}$ and $RL_{before}$ are luminance values of the acquired fluorescence image and reference image,
A and B are constants, $$x:y = c:(a-m) = d:(b-n) \qquad (4),$$

a is an exponent obtained by applying a power approximation to a characteristic of luminance versus distance from the illumination portion to the subject, for the fluorescence image obtained by a fluorescence imaging unit when excitation light of a predetermined intensity is radiated toward the subject, b is an exponent obtained by applying a power approximation to a characteristic of luminance versus cosine from the illumination portion to the subject, for the fluorescence image obtained by the fluorescence imaging unit when excitation light of a predetermined intensity is radiated toward the subject, c is an exponent obtained by applying a power approximation to a characteristic of luminance versus distance from the illumination portion to the subject, for the reference image obtained by a return-light imaging unit when illumination light of a predetermined intensity is radiated toward the subject, d is an exponent obtained by applying a power approximation to a characteristic of luminance versus cosine from the illumination portion to the subject, for the reference image obtained by the return-light imaging unit when illumination light of a predetermined intensity is radiated toward the subject, $$r_D^{|m|} \cdot r_\theta^{|n|} \leq 1 + e_{max} \qquad (3),$$

$r_D = D_{max}/D_{min}$,
$r_\theta = \cos\theta_{min}/\cos\theta_{max}$,
$D_{max}$ is a presumed maximum observation distance,
$D_{min}$ is a presumed minimum observation distance,
$\theta_{max}$ is a presumed maximum observation angle,
$\theta_{min}$ is a presumed minimum observation angle (where, $0° \leq \theta_{min} < \theta_{max} \leq 90°$),
m and n are arbitrary constants that satisfy Expression (4) and Expression (3),
$e_{max}$ is $(FL_{after}/RL_{after})_{max} \div (FL_{after}/RL_{after})_{min} - 1$,
$(FL_{after}/RL_{after})_{max}$ is a maximum value within a range from the presumed minimum observation distance to the presumed maximum observation distance and within a range from the presumed minimum observation angle to the presumed maximum observation angle, and
$(FL_{after}/RL_{after})_{min}$ is a minimum value within a range from the presumed minimum observation distance to the presumed maximum observation distance and within a range from the presumed minimum observation angle to the presumed maximum observation angle.

DESCRIPTION OF EMBODIMENTS

A fluoroscopy apparatus 1 and a fluoroscopy method according to an embodiment of the present invention will be described below with reference to the drawings.

Figure 1:
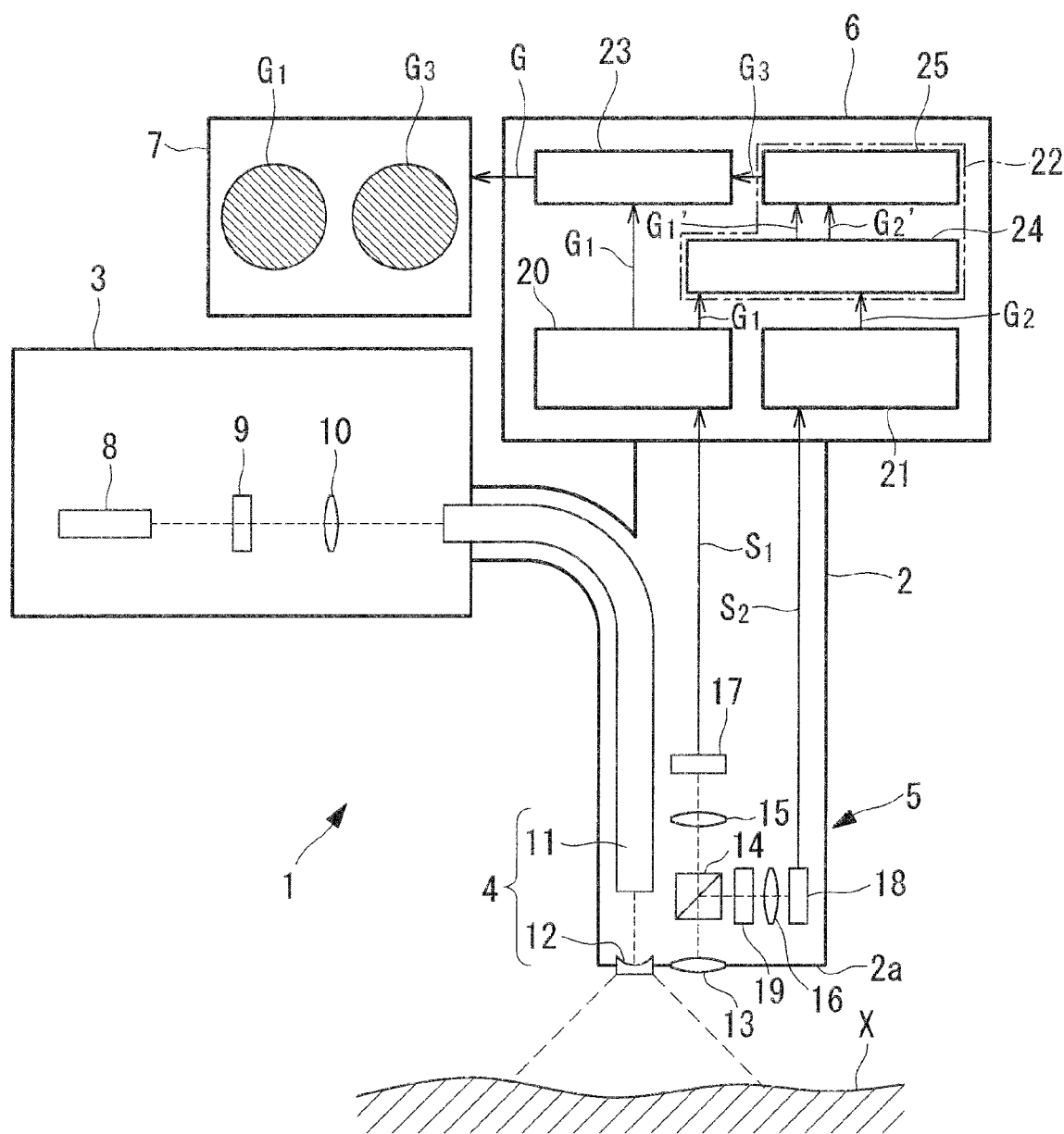
FIG. 1 is a diagram showing the overall configuration of a fluoroscopy apparatus according to an embodiment of the present invention.

As shown in FIG. 1, the fluoroscopy apparatus 1 according to this embodiment is an endoscopic device and is provided with a long, thin inserted portion 2 that is inserted into a body; a light source (illumination portion) 3; an illumination unit (illumination portion) 4 that radiates illumination light and excitation light coming from the light source 3 toward an subject X from a distal end of the inserted portion 2; an image-acquisition unit 5 that is provided at the distal end of the inserted portion 2 and that acquires image information of biological tissue, that is, the subject X; an image-processing unit 6 that is disposed at the base of the inserted portion 2 and that processes the image information acquired by the image-acquisition unit 5; and a monitor 7 that displays an image G that has been processed by the image-processing unit 6.

The light source 3 is provided with a xenon lamp 8, a filter 9 that extracts the excitation light and the illumination light (for example, a wavelength band between 400 and 740 nm) from the illumination light emitted from the xenon lamp 8, and a coupling lens 10 that focuses the excitation light and the illumination light that have been extracted by the filter 9.

The illumination unit 4 is provided with a light-guide fiber 11 that is disposed along a longitudinal direction of the inserted portion 2 over nearly the entire length thereof and that guides the excitation light and the illumination light focused by the coupling lens 10, and an illumination optical system 12 that is provided at the distal end of the inserted portion 2, that spreads the excitation light and the illumination light guided by the light guide fiber 11, and that irradiates the subject X facing an end face 2a of the inserted portion 2.

The image-acquisition unit 5 is provided with an objective lens 13 that collects return light returning from a predetermined observation region of the subject X; a dichroic mirror (splitting portion) 14 that reflects light of the excitation wavelength or higher (excitation light and fluorescence) in the return light collected by the objective lens 13 and transmits the illumination light having a shorter wavelength than the excitation wavelength; two focusing lenses (image-acquisition optical systems) 15 and 16 that respectively focus the illumination light transmitted through the dichroic mirror 14 and the fluorescence reflected at the dichroic mirror 14; and two image acquisition devices 17 and 18, such as CCDs, that images the fluorescence and the illumination light focused by the focusing lenses 15 and 16. In the figures, reference sign 19 is an excitation-light cut filter that blocks (transmits only light in, for example, a wavelength band between 760 and 850 nm) the excitation light in the light reflected at the dichroic mirror 14.

The image-processing unit 6 is provided with a reference-image generating unit 20 that generates a reference image $G_1$ from reference image information $S_1$ acquired by the image acquisition device 17; a fluorescence-image generating unit 21 that generates a fluorescence image $G_2$ from fluorescence image information $S_2$ acquired by the image acquisition device 18; an image-correcting unit 22 that generates a corrected fluorescence image $G_3$ on the basis of the reference image $G_1$ and the fluorescence image $G_2$ generated by the reference-image generating unit 20 and the fluorescence-image generating unit 21; and an image-combining unit 23 that generates an image G by combining the corrected fluorescence image $G_3$ generated at the image-correcting unit 22 and the reference image $G_1$ generated at the reference-image generating unit 20.

The image-combining unit 23 is configured to synthesize the image G so that, for example, the reference image $G_1$ and the corrected fluorescence image $G_3$ are simultaneously displayed side-by-side on the monitor 7, and output it to the monitor 7.

Here, as the fluorescence image $G_2$, for example, a fluorescence image from a fluorochrome Cy7 may be employed. In particular, if a tumor-specific fluorescent agent, for example, a fluorescent agent formed by causing Cy7 to bind to an antibody to a cancer-specific molecule CEA (Anti-CEA antibody) is administered to the subject X in advance, a tumor specific fluorescence image $G_2$ can be obtained. As the reference image $G_1$, an image based on, for example, return light due to the illumination light being reflected at the surface of the subject X and return light due to scattering inside the subject X may be employed.

The image-correcting unit 22 is provided with a preprocessing unit 24 that subjects the reference image $G_1$ generated by the reference-image generating unit 20 and the fluorescence image $G_2$ generated by the fluorescence-image generating unit 21 to preprocessing, and a division processing unit 25 that divides a fluorescence image $G_2$' subjected to preprocessing in the preprocessing unit 24 by a reference image $G_1$' subjected to preprocessing therein.

The preprocessing unit 24 is configured to realize the following image processing method.

$$FL_{after} = A \times FL_{before}^{x} \tag{5}$$

$$RL_{after} = B \times RL_{before}^{y} \tag{6}$$

where $FL_{before}$ and $RL_{before}$ are luminance values of the acquired fluorescence image $G_2$ and reference image $G_1$;

$FL_{after}$ and $RL_{after}$ are luminance values of the preprocessed fluorescence image $G_2$' and reference image $G_1$';

A and B are constants; and x and y are exponents that are determined in advance by the following method.

The method for setting the exponents x and y will be described below.

The fluorescence image $G_2$ and the reference image $G_1$ generally have approximately the following dependencies on observation distance D and observation angle θ.

$$FL_{before} \propto D^a \cos^b\theta \text{ and } RL_{before} \propto D^c \cos^d\theta.$$

Dividing the first expression by the second expression without modification gives $$FL_{before}/RL_{before} \propto D^{a-c} \cos^{b-d}\theta.$$

where the observation distance D can be taken as, for example, the distance from the distal end of the inserted portion 2 to the surface of the subject X, and the observation angle θ can be taken as, for example, an angle formed between a normal at the surface of the subject X and an optical axis of the objective lens 13 (or the longitudinal direction of the inserted portion 2).

Next, raising the luminance values of the fluorescence image $G_2$ and the reference image $G_1$ to the power of the exponents x and y, respectively, yields $$FL_{before}{}^x/RL_{before}{}^y \propto D^{ax-cy} \cos^{bx-dy}\theta.$$

Therefore, the exponents x and y are set so that, with m=ax−cy and n=bx−dy, m and n serve as permissible limits.
In other words, $$x=(cn-dm)/(bc-ad) \quad (1)$$

$$y=(an-bm)/(bc-ad) \quad (2)$$

and when the denominator bc−ad=0, the exponents x and y are set so that x:y=c:a=d:b.

Assuming a presumed maximum observation distance is $D_{max}$, a presumed minimum observation distance is $D_m$, a presumed maximum observation angle is $\theta_{max}$, and a presumed minimum observation angle is $\theta_{min}$ (0°≦$\theta_{min}$<$\theta_{max}$≦90°), respective ratios $r_D$ and $r_\theta$ are $$r_{max}=D_{max}/D_{min} \text{ and } r_\theta=\cos\theta_{min}/\cos\theta_{max}$$

and, by using a maximum permissible error rate $\theta_{max}$ in the corrected fluorescence image, m and n are selected so that $$r_D{}^{|m|} \cdot r_\theta{}^{|n|} \leq 1+e_{max} \quad (3).$$

Here, the presumed range of the observation distance D can be determined from, for example, the depth of field of the objective lens 13, and the presumed range of the observation angle θ can be determined from, for example, the angular field of view of the objective lens 13.
$e_{max}$ can be obtained from $$(FL_{after}/RL_{after})_{max} \div (FL_{after}/RL_{after})_{min} = 1+e_{max}.$$

Therefore, first, the maximum permissible error rate $e_{max}$ should be set in advance; next, m and n that satisfy Expression (3) should be set; and x and y that satisfy Expression (1) and Expression (2) on the basis of the set m and n should be set.

Exponents a to d are obtained as follows.

Specifically, averages of luminance values of predetermined areas in the fluorescence image $G_2$ and the reference image $G_1$ acquired by irradiating the subject X with the excitation light and the illumination light from the illumination unit 4 while changing the distance D from the illumination unit 4 to the subject X are plotted against the distance D. In this way, the exponents a and c that indicate the dependency on the observation distance D are obtained by performing a power approximation for the obtained distance characteristic, that is, by regression to power functions $D^a$ and $D^c$.

Similarly, for the exponents b and d for the observation angle θ, averages of luminance values of predetermined areas in the fluorescence image $G_2$ and the reference image $G_1$ acquired by irradiating the subject X with the excitation light and the illumination light from the illumination unit 4 while changing the angle θ between the optical axis of the illumination unit 4 and the subject X are plotted against the cosines of the angles, cos θ. In this way, the exponents b and d that indicate the dependency on the observation angle θ are obtained by performing a power approximation for the obtained cosine characteristic, that is, by regression to power functions $\cos^b\theta$ and $\cos^d\theta$.

In the division processing unit 25, the following division is performed using the luminance value $FL_{after}$ of the fluorescence image $G_2'$ and the luminance value $RL_{after}$ of the reference image $G_1'$, which have been subjected to the above preprocessing at each pixel, to obtain a luminance value $FL_{revised}$ of the corrected fluorescence image $G_3$.

$$FL_{revised}=FL_{after}/RL_{after}$$

With the thus-configured fluoroscopy apparatus 1 and fluorescence-image processing method according to this embodiment, dependencies on the observation distance D and the observation angle θ that are mutually different in the fluorescence image $G_2$ and the reference image $G_1$ can be satisfactorily reduced within the range of a predetermined permissible error. Therefore, an advantage is afforded in that a corrected fluorescence image $G_3$ having high quantitativeness can be obtained and that observation can be performed with superior precision.

Furthermore, it is possible to proactively prevent a loss of quantitativeness in the fluorescence image $G_3$ caused by setting inappropriate x and y which increases the values of m and n.

In this embodiment, m and n that yield $r_D{}^{|m|} \cdot r_\theta{}^{|n|} \leq 1+e_{max}$ are selected; however, considering that the absolute values of the exponents a and c, which express the distance dependency, are generally larger than the absolute values of the exponents b and d, x and y may be set so that m is equal to zero.

By doing so, the dependency on the observation distance, which has a large influence, can be eliminated; the dependency on the observation angle can be kept within a range of the permissible error; and fluoroscopy can be performed with even greater quantitativeness.

For example, the angular field of view of a digestive-organ endoscope is generally about 75° on one side. Therefore, θ can be assumed to be about 75° even at its maximum. In addition, assuming that the maximum permissible error rate $e_{max}$ is kept at about 10% within this range, $$r_\theta=\cos\theta_{min}/\cos\theta_{max}=\cos 0°/\cos 75°=3.86.$$

Therefore, $$n=\log(1+0.1)/\log 3.86=0.07.$$

For example, using the exponents a to d obtained by an example experiment, described later, which are
a=−1.518, b=0.514, c=−1.605, d=0.675,
yields x≈0.563 and y≈0.532.

By correcting the fluorescence image $G_2$ by using the exponents x and y obtained in this way, it is possible to obtain a fluorescence image $G_3$ in which the distance dependency is eliminated and the variation in luminance due to the angular dependency is reduced to 10% or less.

In this embodiment, the fluorescence image $G_2$ and the reference image $G_1$ acquired by the image acquisition devices 18 and 19 include noise due to dark current and read-out at the image acquisition devices 18 and 19. If a pixel with zero luminance exists in the reference image $G_1$ when performing the division processing, the division result goes to infinity and an appropriate correction cannot be performed.

Therefore, at the preprocessing unit 24, the fluorescence image $G_2$ may be offset so as to remove noise components due to dark current and read-out, and the reference image $G_1$ may be offset so as to remove noise components due to dark current and read-out and, additionally, to make luminance value of the pixels non-zero values.

In addition to an image obtained from observing surface reflected light and scattered return light from the subject X, the reference image $G_1$ may be an image obtained from observing autofluorescence generated from the subject X and an image obtained from observing fluorescence from another fluorescent agent having fluorescence characteristics of a different wavelength band from the fluorescent agent employed to acquire the fluorescence image $G_2$.

For the images to be displayed on the monitor 7, a white-light reflected image, which is separately acquired, may be displayed as the image to be displayed next to the corrected fluorescence image $G_3$ instead of the reference image G1.

For both the reference image $G_1$ and the fluorescence image $G_2$, the degrees of dependency on the observation distance D and observation angle θ are influenced by surface roughness of the subject X, the thickness of a lesion and tissue thereof, absorption thereof, scattered return light at the interior of the subject X, and so on. Since the characteristics of absorption by blood, etc. in the tissue and the subject X or the characteristics of scattering caused in the tissue differ depending on the wavelength of light, the degrees of dependency of the reference image $G_1$ on the observation distance D and the observation angle θ can be changed by selecting the wavelength. That is, by selecting the wavelength of the illumination light, the exponents a to d can be adjusted.

If m and n are set as m=n=0 for m=ax−cy and n=bx−dy, because no solution other than x=y=0 exists, such a setting is normally not possible.

However, if the wavelength of the illumination light can be set so as to obtain the dependency on the observation distance D or the dependency on the observation angle θ such that $\epsilon$=0 where ad−bc=$\epsilon$, even if m and n are set as m=n=0 for m=ax−cy and n=bx−dy, x and y that yield x:y=c:a=d:b can be set.

Therefore, it is preferable that the wavelength of the illumination light be set so that $\epsilon$=0, or as close to zero as possible. By doing so, the dependencies on both the observation distance D and the observation angle θ can be almost entirely eliminated in the corrected fluorescence image $G_3$, and the quantitativeness of the fluorescence image $G_3$ can be enhanced as much as possible.

Figure 2:
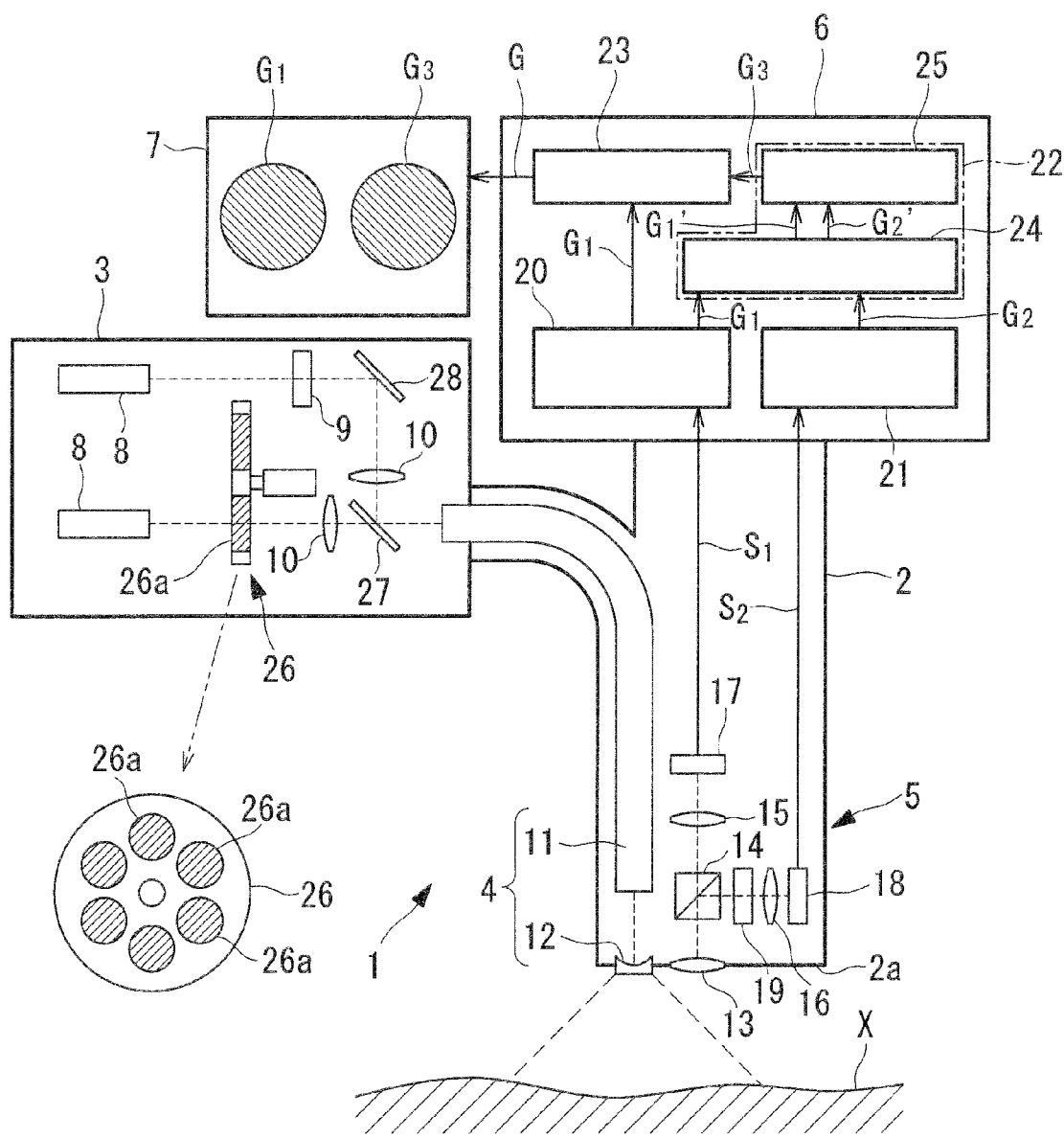
FIG. 2 is a diagram showing the overall configuration of a first modification of the fluoroscopy apparatus in FIG. 1.

Therefore, as shown in FIG. 2, to select the wavelength of the illumination light in the excitation light and the illumination light emitted from the xenon lamp 8, a filter turret 26 that can alternately dispose a plurality of filters 26a having differing transmittance characteristics on the optical axis may be provided, $\epsilon$ may be calculated while changing the wavelength, and a wavelength that minimizes the absolute value of $\epsilon$ may be selected. In the figure, reference sign 27 is a dichroic mirror that multiplexes the excitation light, and the illumination light and reference sign 28 is a mirror.

Figure 3:
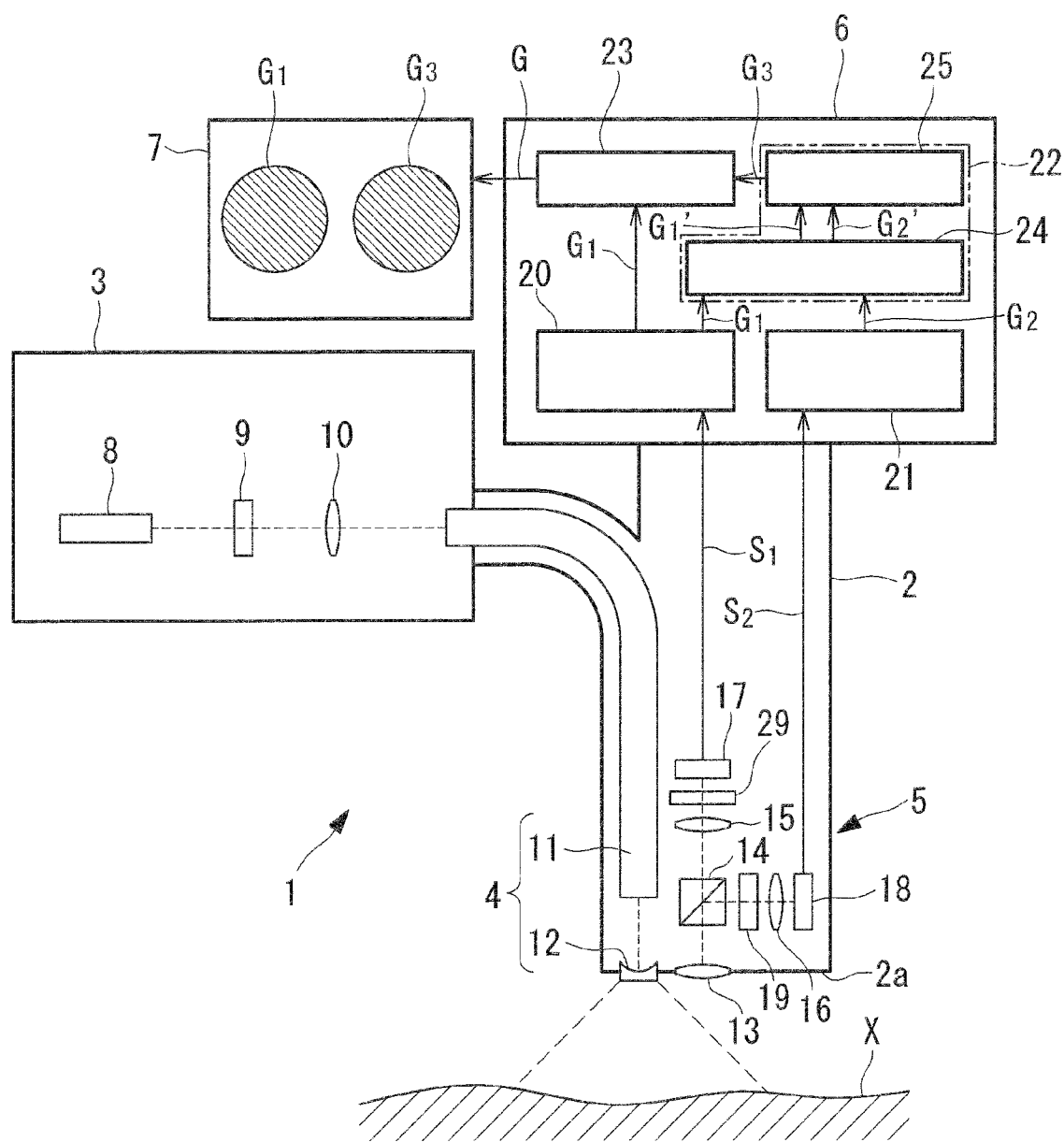
FIG. 3 is a diagram showing the overall configuration of a second modification of the fluoroscopy apparatus in FIG. 1.

As shown in FIG. 3, the exponents a to d can also be optimized by providing an adjustable diaphragm 29 at a subsequent stage of the objective lens 13 and by adjusting the aperture of the objective lens 13 with it. Observed light includes a large amount of light returning from the subject X after being scattered therein in addition to light reflected at the surface of the subject X. If the aperture of the objective lens 13 is large, light that has underwent multiple scattering and is propagated from a point that is distant from the optical axis can also be taken in. That is, the larger the aperture, the larger the contribution of light returning from the interior of the subject X. Since the ratio of light reflected at the surface of the subject X and the return light from inside thereof is correlated with the dependencies on the observation distance D and the observation angle θ, the exponents a to d can be adjusted by adjusting the aperture.

Figure 4:
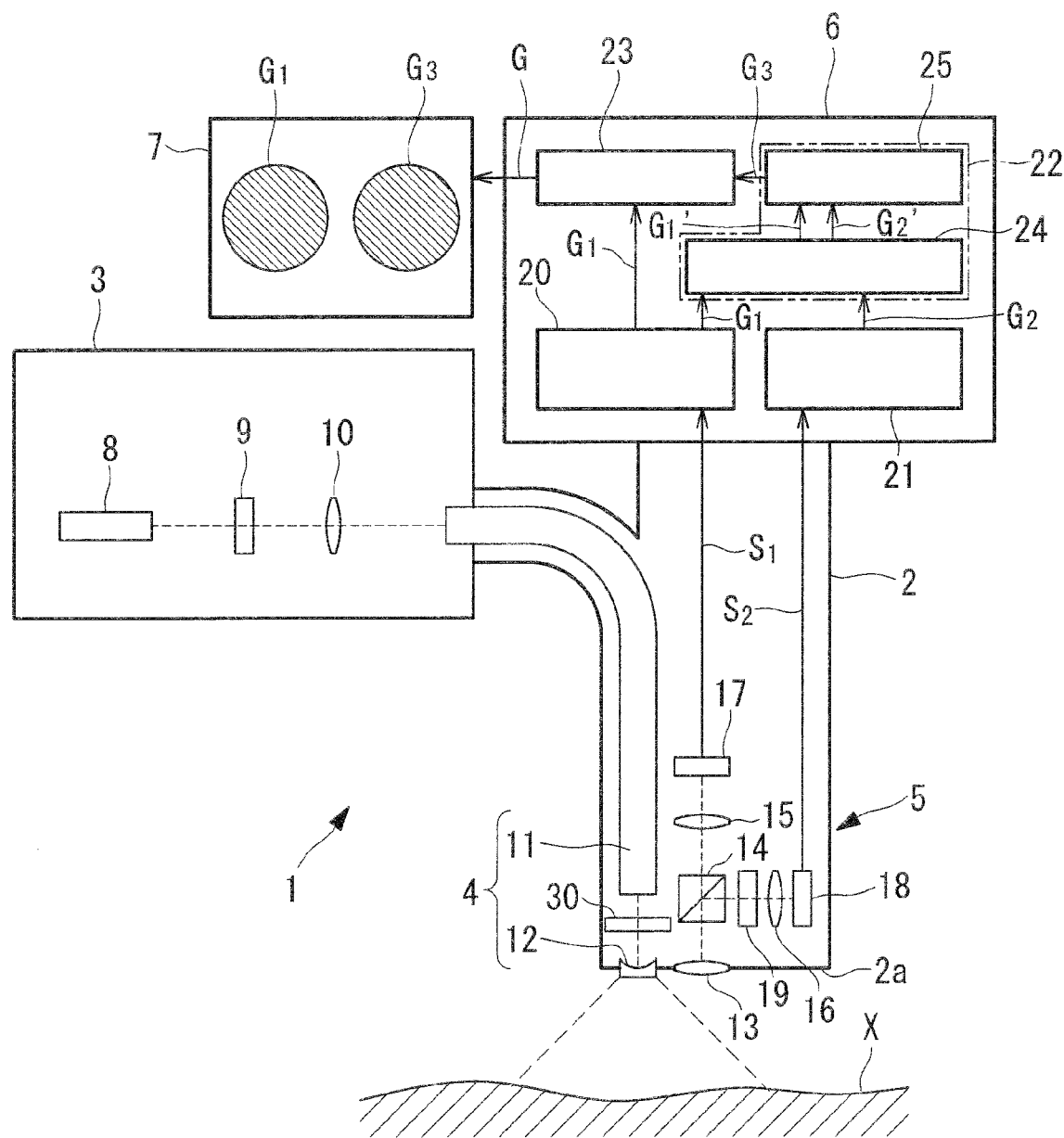
FIG. 4 is a diagram showing the overall configuration of a third modification of the fluoroscopy apparatus in FIG. 1.

As shown in FIG. 4, the illumination unit 4 may be provided with an adjustable diaphragm 30. For example, when the aperture is a point, illuminance at the subject X is inversely proportional to the square of the distance; however, when it is not a point, the relationship departs from one that is inversely proportional to the square of the distance.

Figure 5:
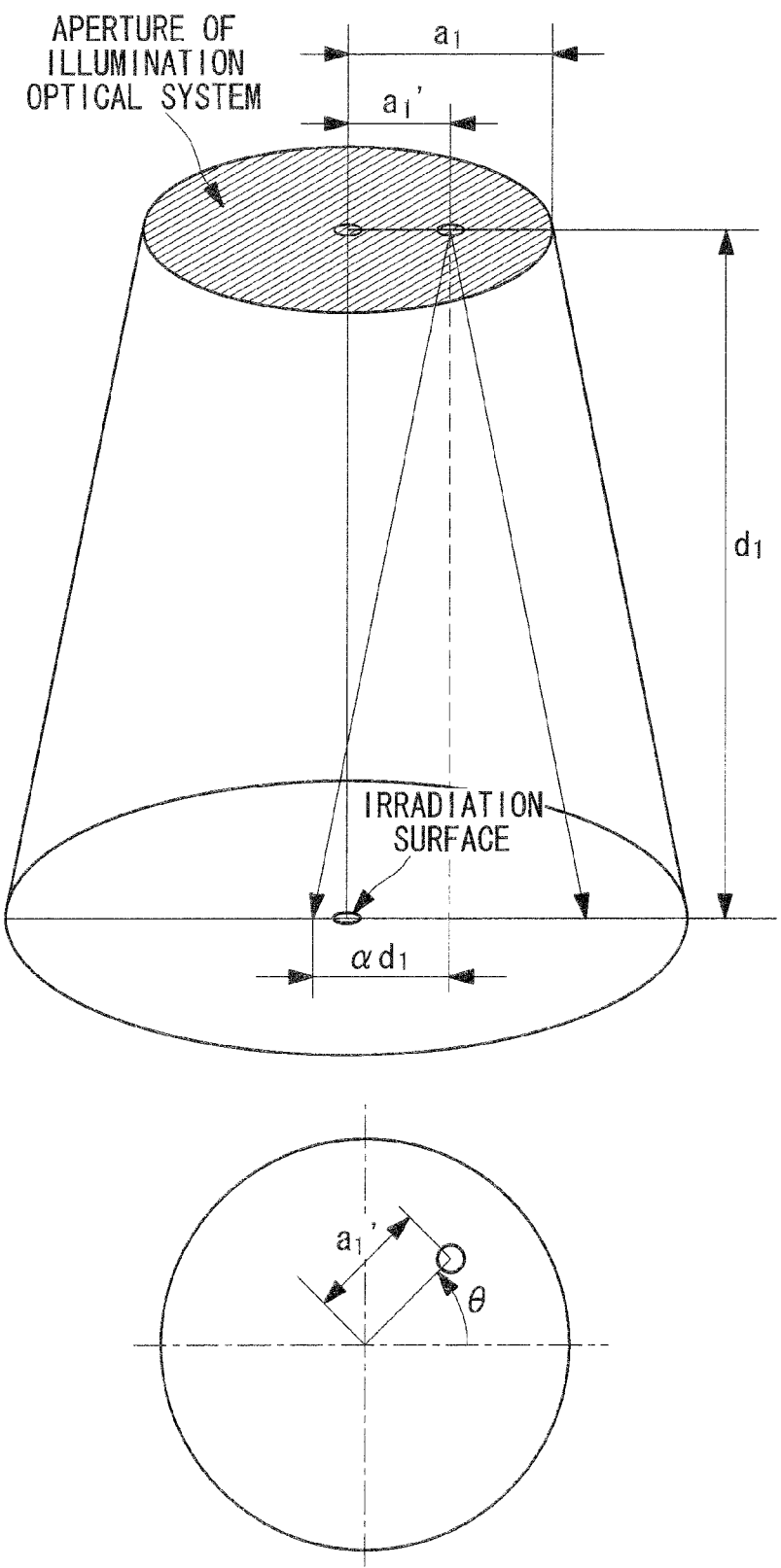
FIG. 5 is a diagram for explaining the relationship between illuminance at an irradiation surface of a subject and distance thereto, when an aperture has a finite size.

Here, the relationship between the illuminance at an irradiation surface of the subject X and the distance thereto is considered as an example for a case in which the illumination light has a Gaussian distribution centered on the optical axis and the aperture has a finite size. As shown in FIG. 5, for the irradiation surface of the subject X that is on the optical axis of the illumination light and that is separated from the aperture of the illumination optical system 12 by distance $d_1$, changes in illuminance and distance are considered. Radius $a_1$ for the aperture and distance $d_1$ are assumed. Here, illuminance is expressed based on light emitted from an area on the plane of the aperture of the illumination optical system, which is separated from the optical axis by $a_1'$ to $a_1'+da_1'$ and has angles of θ to θ+dθ, reaching the irradiation surface. The angle θ is defined as shown in a lower figure (a figure in which the aperture of the illumination optical systems is viewed from below) of FIG. 5. Two one-dot-chain lines are straight lines that intersect with the optical axis of the illumination optical system and that are perpendicular to each other. In terms of a constant α that is proportional to the divergence of the illumination light and the total intensity E of the illumination light, the illuminance at the irradiation surface can be expressed as follows.

$$\text{illuminance} = \frac{E}{\pi a_1^2} \cdot \frac{\beta}{\pi a_1^2 d_1^2} \cdot \exp\left(-\frac{\beta}{\alpha^2 d_1^2} a_1'^2\right) da_1' \cdot a_1' d\theta \quad \{\text{Formula 1}\}$$

Here, β is a constant (positive real number) that is related to the Gaussian half-width (the larger β, the smaller the half-width). Therefore, the total illuminance, which is the sum of illuminances when light emitted from all points in the aperture reaches the irradiation surface, can be expressed as follows.

$$\text{total illuminance} = \int_0^{2\pi\alpha} \int_0^\alpha \frac{E}{\pi a_1^2} \cdot \frac{1}{d_1} \exp\left(-\frac{\beta}{\alpha^2 d_1^2} a_1'^2\right) da_1' \cdot a_1' d\theta \quad \{\text{Formula 2}\}$$

$$= \frac{E}{\pi a_1^2}\left(1 - \exp\left(-\frac{\beta}{\alpha^2 d_1^2} a_1^2\right)\right)$$

Here, if exponents of the exponential function are approximated up to the fourth-power term, the total illuminance can be expressed as follows.

$$\text{total illuminance} \cong \frac{\beta E}{\pi \alpha^2}\left(\frac{1}{d_1^2} - \frac{\alpha_1^2 \beta}{2\alpha^2} \cdot \frac{1}{d_1^4}\right) \quad \{\text{Formula 3}\}$$

According to Formula 3, the larger the aperture, the larger the contribution of a term that is inversely proportional to the fourth power of the distance $d_1$, thus departing from the characteristic that the total illuminance is inversely proportional to the square of the distance. Although a simple power function is not applicable in this case, an approximate value can be obtained by obtaining an approximation curve by the least squares method or the like.

Figure 6A:
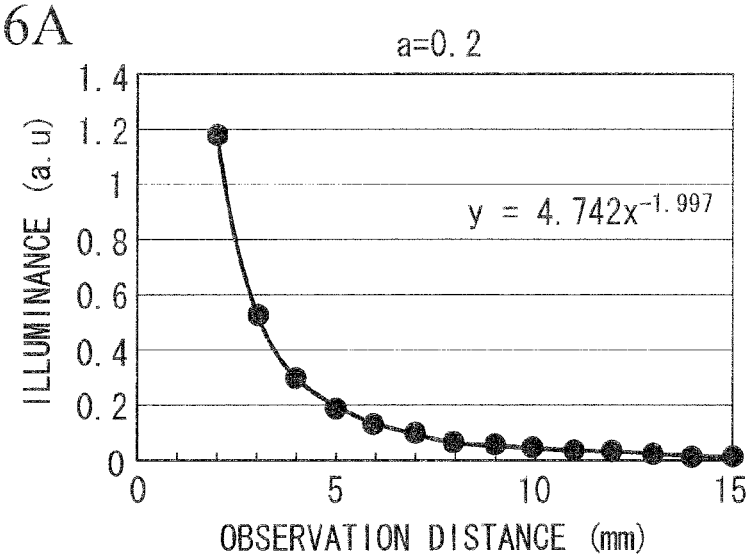
FIG. 6A is a diagram showing a graph in which a power approximation is applied to an illuminance-vs.-observation distance characteristic obtained under a predetermined condition when the aperture diameter in FIG. 5 is changed.
Figure 6B:
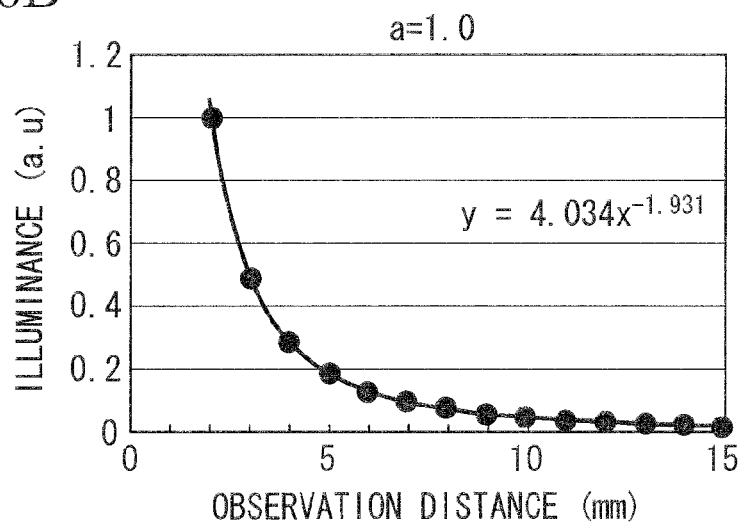
FIG. 6B is a diagram showing a graph in which a power approximation is applied to an illuminance-vs.-observation distance characteristic obtained under the predetermined condition when the aperture diameter in FIG. 5 is changed.
Figure 6C:
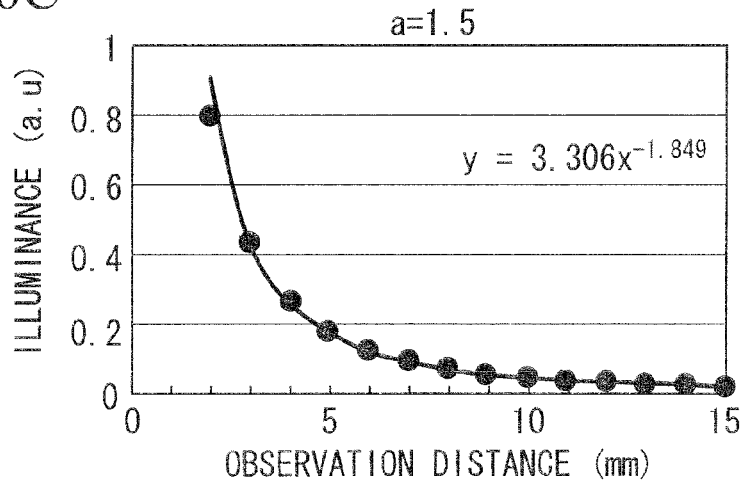
FIG. 6C is a diagram showing a graph in which a power approximation is applied to an illuminance-vs.-observation distance characteristic obtained under the predetermined condition when the aperture diameter in FIG. 5 is changed.

For example, assuming that E=10, α=1, and β=1.5, when regression curves at observation distances 2 to 15 are individually calculated by setting $a_1$ to 0.2, 1, and 1.5, approximations can be made with functions that are proportional to the −1.997th power, the −1.931th power, and the −1.849th power of the distance, as shown in FIG. 6A to 6C.

By doing so, fluoroscopy with greater quantitativeness can be performed.

Figure 7:
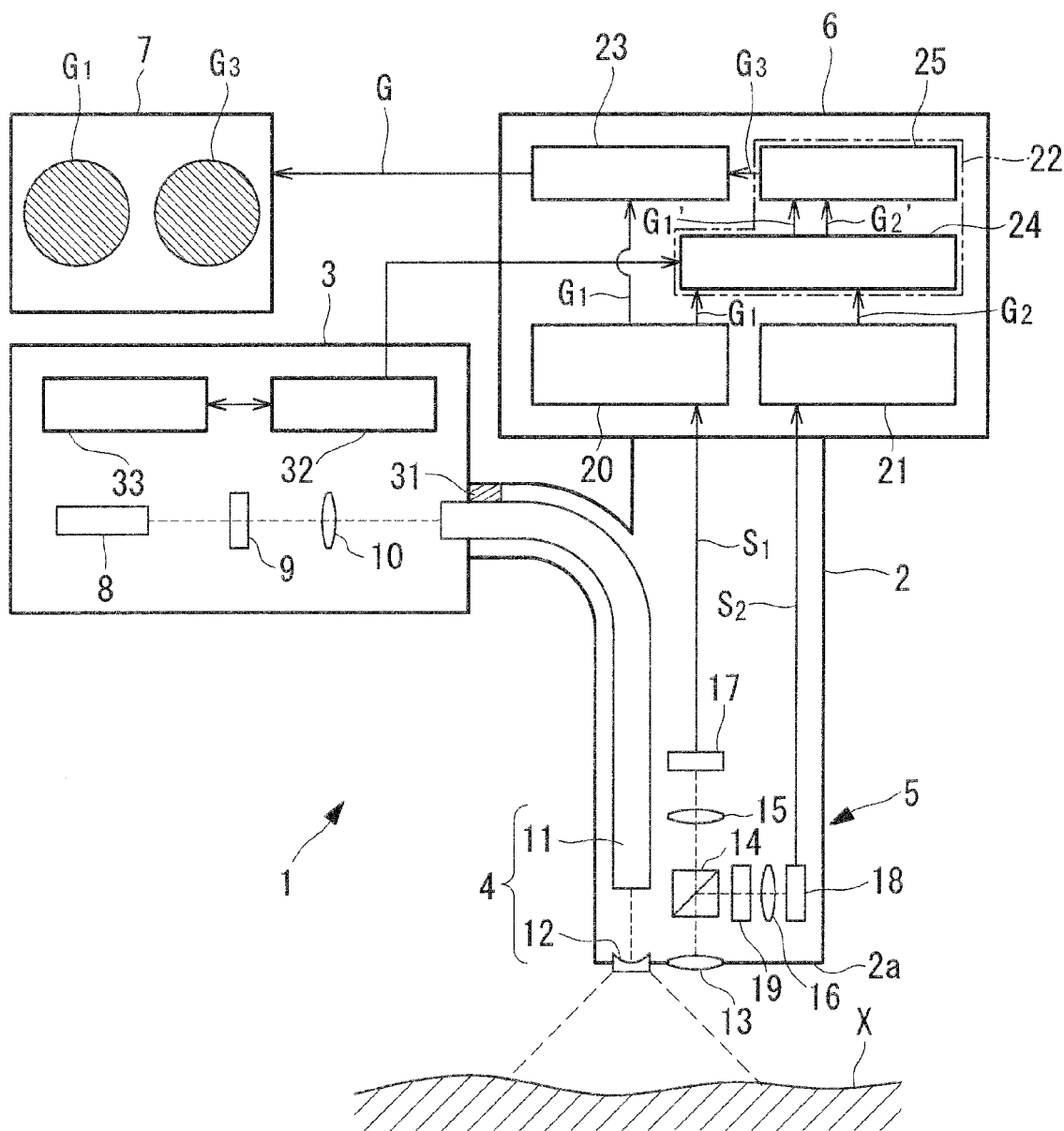
FIG. 7 is a diagram showing the overall configuration of a fourth modification of the fluoroscopy apparatus in FIG. 1.

As shown in FIG. 7, in this embodiment, the inserted portion (attachable/detachable part) 2 may be provided so as to be attachable/detachable to/from the light source 3. In this case, by detaching the inserted portion 2 and by exchanging it with another inserted portion 2, various optical system included in the inserted portion 2, including the objective lens 13, are changed; therefore, the above-described exponents a to d change due to changes in numerical aperture (NA), pupil diameter, etc. of the objective lens 13 or changes in the fluorescence wavelength that is detected, the fluoroscopy target site (stomach tissue, large intestine tissue, etc.), and so on.

Therefore, preferably, the inserted portion 2 is provided with an IC chip 31 that stores identification information and, on the light source 3 side to which the inserted portion 2 is attached, a reading device 32 that reads the identification information in the IC chip 31 and a storage unit 33 that stores the identification information in association with exponents x and y appropriate for each inserted portion 2 are provided. Then, it suffices that the preprocessing unit 24 receives the exponents x and y output from the storage unit 33, which correspond to the identification information of the inserted portion 2, and perform the above-described calculation.

By doing so, an advantage is afforded in that, even if the inserted portion 2 for the light source 3 is exchanged, optimal exponents x and y are set for the inserted portion 2, and a fluorescence image $G_3$ having high quantitativeness can always be acquired.

Figure 8:
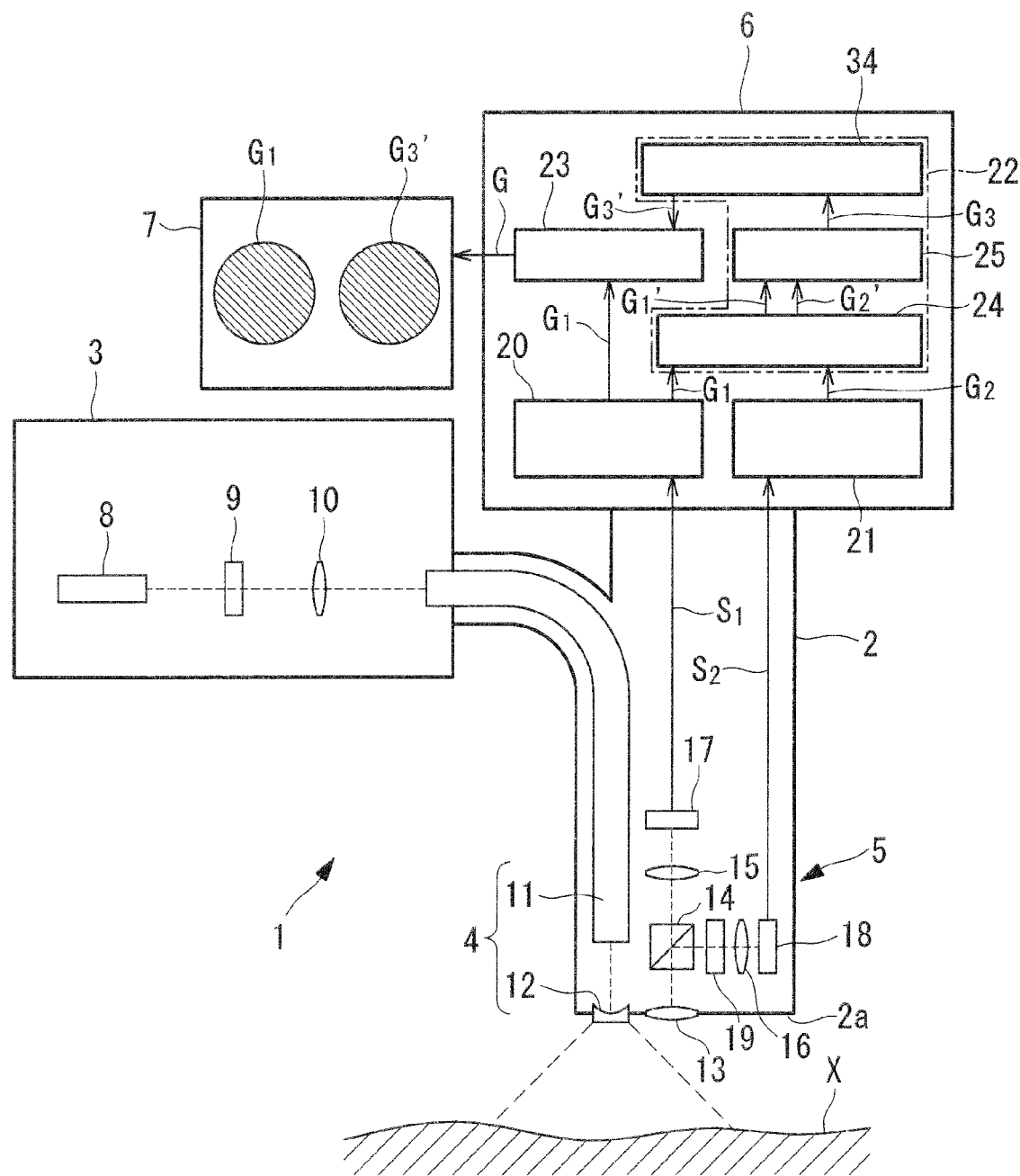
FIG. 8 is a diagram showing the overall configuration of a fifth modification of the fluoroscopy apparatus in FIG. 1.

As shown in FIG. 8, a post-processing unit 34 that calculates a fluorescence image $G_3'$ by additionally raising the divided value obtained by the division processing unit 25 to the $1/x^{th}$ power may be provided. By doing so, it is possible to maintain the proportional relationship between the luminance value of a finally obtained corrected fluorescence image and the concentration of a fluorescent substance contained in the subject.

The fluorescence intensity of the fluorescence image $G_2$ is proportional to the concentration of a fluorochrome. Specifically, for example, assuming the concentration of a fluorochrome (or fluorescent agent) accumulated in a lesion, etc. as C (mol/L), the volume of the lesion where the fluorochrome is accumulated as V (cm³), and the cross-sectional area of a plane cut parallel to a top surface of the lesion as S (cm²), the luminance E (W/cm²·sr) of fluorescence emitted from the lesion is expressed as $$E \propto CV/S \approx Ct.$$

Here, t (cm) indicates the thickness of the lesion. Therefore, a gradation value $FL_{before}$ of the captured fluorescence image $G_2$ is approximately proportional to the concentration of the fluorochrome accumulated in the lesion and the thickness of the lesion. In other words, approximately, $FL_{before} \propto Ct$.

However, as described above, in the case of preprocessing that raises the luminance value of fluorescence image $G_2$ to the power of exponent x, a gradation value $FL_{revised}$ of the corrected fluorescence image $G_3$ and Ct have a relationship $$FL_{revised} \propto (Ct)^x,$$

and thus, the fluorescence image $G_3$ does not linearly express the fluorescence concentration in cases other than x=1. Thus, by raising to the $1/x^{th}$ power at the post-processing unit 34, the fluorescence image $G_3'$ that linearly expresses the fluorescence concentration can be acquired. Therefore, the quantitativeness of the fluorescence image can be increased, and the fluorescence concentration and the thickness of a lesion where a fluorochrome has accumulated can also be reflected more accurately.

In this case, because it is preferable that the dependencies on the observation distance D and the observation angle θ be eliminated, including the post-processing by the post-processing unit 34, instead of m=ax−cy and n=bx−dy in the above-described example, m=(ax−cy)/x and n=(bx−dy)/x may be used, and the exponents x and y may be set so that m and n serve as permissible limits.

Here, in order for these expressions to have solutions other than x=y=0 regarding x and y, it is necessary to satisfy $$x:y=c:(a-m)=d:(b-n) \qquad (4).$$

Therefore, m and n that satisfy Expression (4) and Expression (3) are set, and, on the basis of the set m and n, x and y should be set from Expression (4).

In this case, when m is set to 0, if ε=ad−bc, from Expression (4), n=(bc−ad)/c=−ε/c. Therefore, as described above, by adjusting the wavelengths of the reference image $G_1$ and the fluorescence image $G_2$ so that the absolute value of ε is set to be the minimum value thereof, the value of n can be further minimized within a range that satisfies Expression (3), and the dependencies of the corrected fluorescence image $G_3$ on the observation distance D and the observation angle θ are minimized. Here, the configuration may be such that the size of the aperture of the objective lens 13 or the illumination unit 4 is set. With such an adjustment, the quantitativeness of the fluorescence image $G_3$ can be further enhanced as much as possible.

Specifically, if the wavelength of the illumination light or the size of the aperture of the objective lens 13 or the illumination unit 4 can be set so that the dependency on the observation distance D or the dependency on the observation angle θ that makes ε=0 can be obtained, from Expression (4), x and y can be set so that m=n=0 and x:y=c:a=d:b; therefore, the dependencies of the corrected fluorescence image $G_3$ on the observation distance D and the observation angle θ can both be eliminated, and the error can be made almost zero.

Next, a fluoroscopy system 40 according to an embodiment of the present invention will be described below with reference to the drawings.

In the description of this embodiment, portions that are common in configuration with the fluoroscopy apparatus 1 according to the above-described embodiment are given the same reference signs, and descriptions thereof are omitted.

Figure 9:
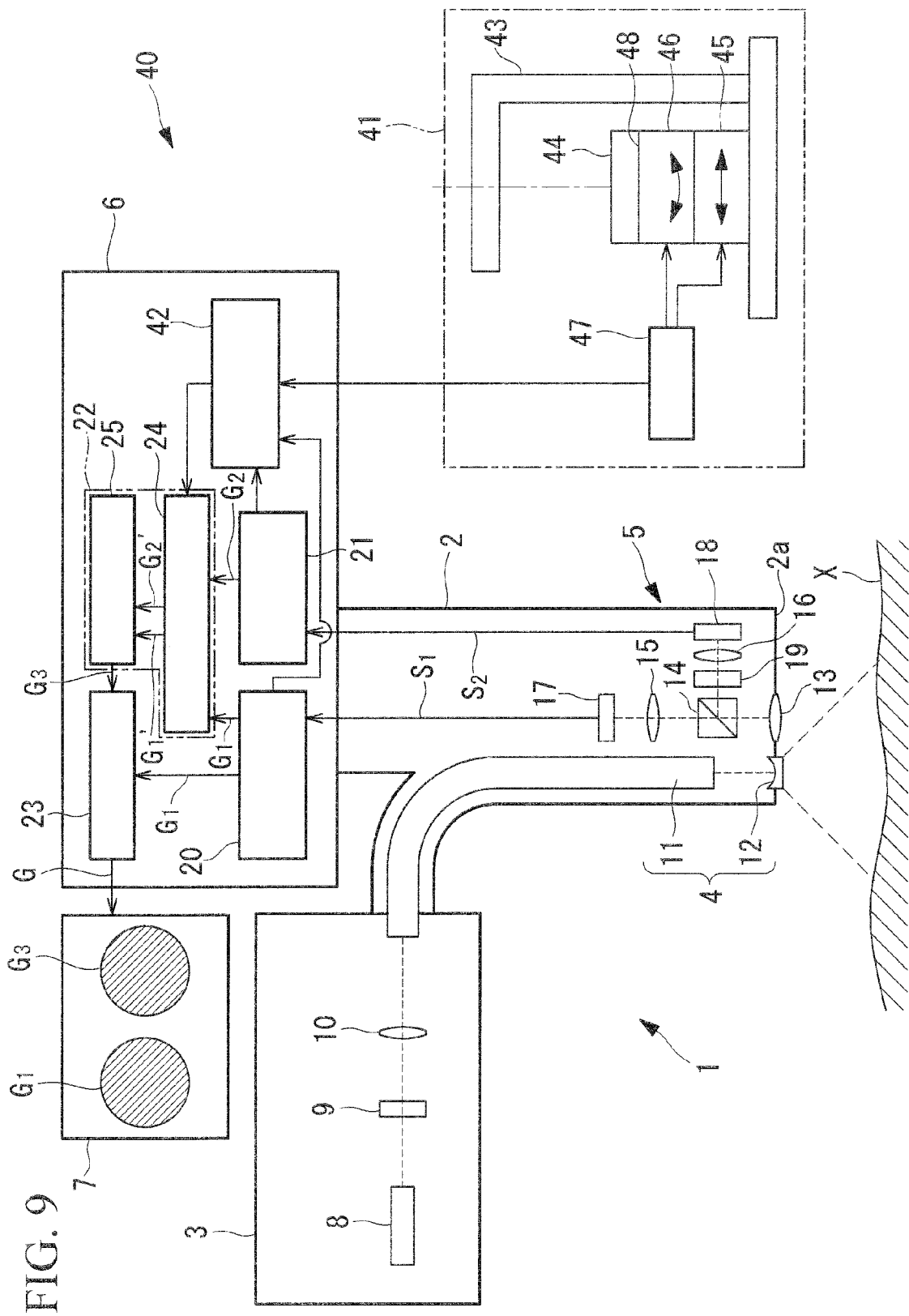
FIG. 9 is a diagram showing the overall configuration of a fluoroscopy system according to an embodiment of the present invention.

As shown in FIG. 9, the fluoroscopy system 40 according to this embodiment is provided with the fluoroscopy apparatus 1 and a calibration device 41 to which the fluoroscopy apparatus 1 is mounted.

In this embodiment, the fluoroscopy apparatus 1 is provided with a dependency-constant determining unit 42 that calculates the exponents x and y on the basis of distance and angle information sent from the calibration device 41, the reference image $G_1$ sent from the reference-image generating unit 20, and the fluorescence image $G_2$ sent from the fluorescence-image generating unit 21.

The dependency-constant determining unit 42 stores a preset maximum permissible error rate $e_{max}$ and a constant m.

The dependency-constant determining unit 42 is configured to sequentially store the distance and angle information sent from the calibration device 41, the reference image $G_1$ sent from the reference-image generating unit 20, and the fluorescence image $G_2$ sent from the fluorescence-image generating unit 21 in association with each other until a predetermined number of datasets are collected. Then, when the predetermined number of datasets are collected, observation distance characteristics and observation angle characteristics are plotted from the luminance values of the fluorescence image $G_2$ and the luminance values of the reference image $G_1$, respectively. Furthermore, the dependency-constant determining unit 42 calculates the exponents a to d by applying a power approximation to the generated observation distance characteristics and observation angle characteristics.

At the point where the exponents a to d are calculated in this way, the constant n is calculated by using the stored maximum permissible error rate $e_{max}$ and constant m, and the exponents x and y are calculated by using these constants m and n and the exponents a to d and are output to the preprocessing unit 24.

Figure 10:
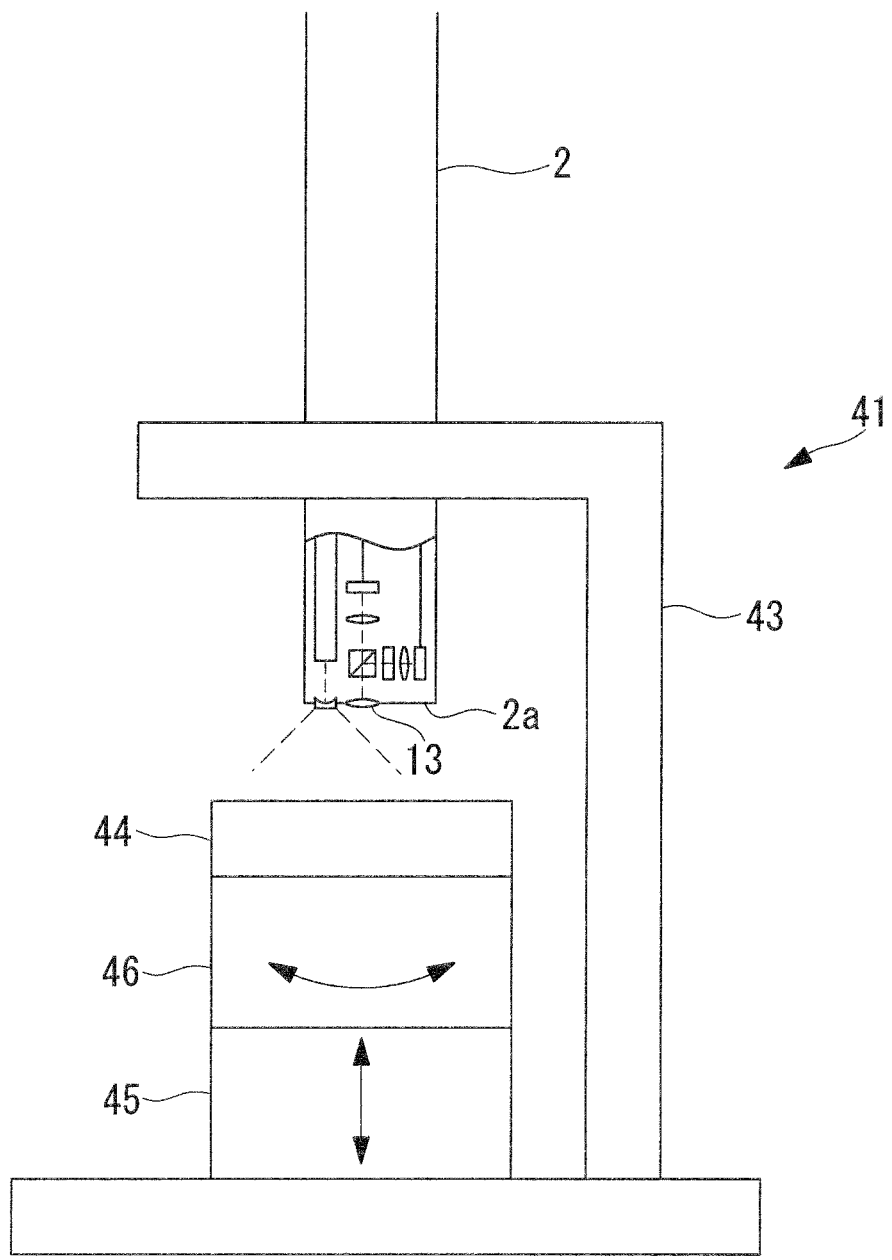
FIG. 10 is a diagram showing a calibration device in the fluoroscopy system in FIG. 9.

As shown in FIGS. 9 and 10, the calibration device 41 is provided with a holder 43 that secures the inserted portion 2; a standard specimen 44 that can be made to oppose the end face 2a of the inserted portion 2 secured in the holder 43 so as to be separated therefrom by the observation distance; a translation stage 45 that changes the observation distance between the end face 2a of the inserted portion 2 and the standard specimen 44; a tilt stage 46 that changes the angle (observation angle) of the surface of the standard specimen 44 relative to the optical axis of the objective lens 13; and a controller 47 that controls these stages 45 and 46.

Figure 11:
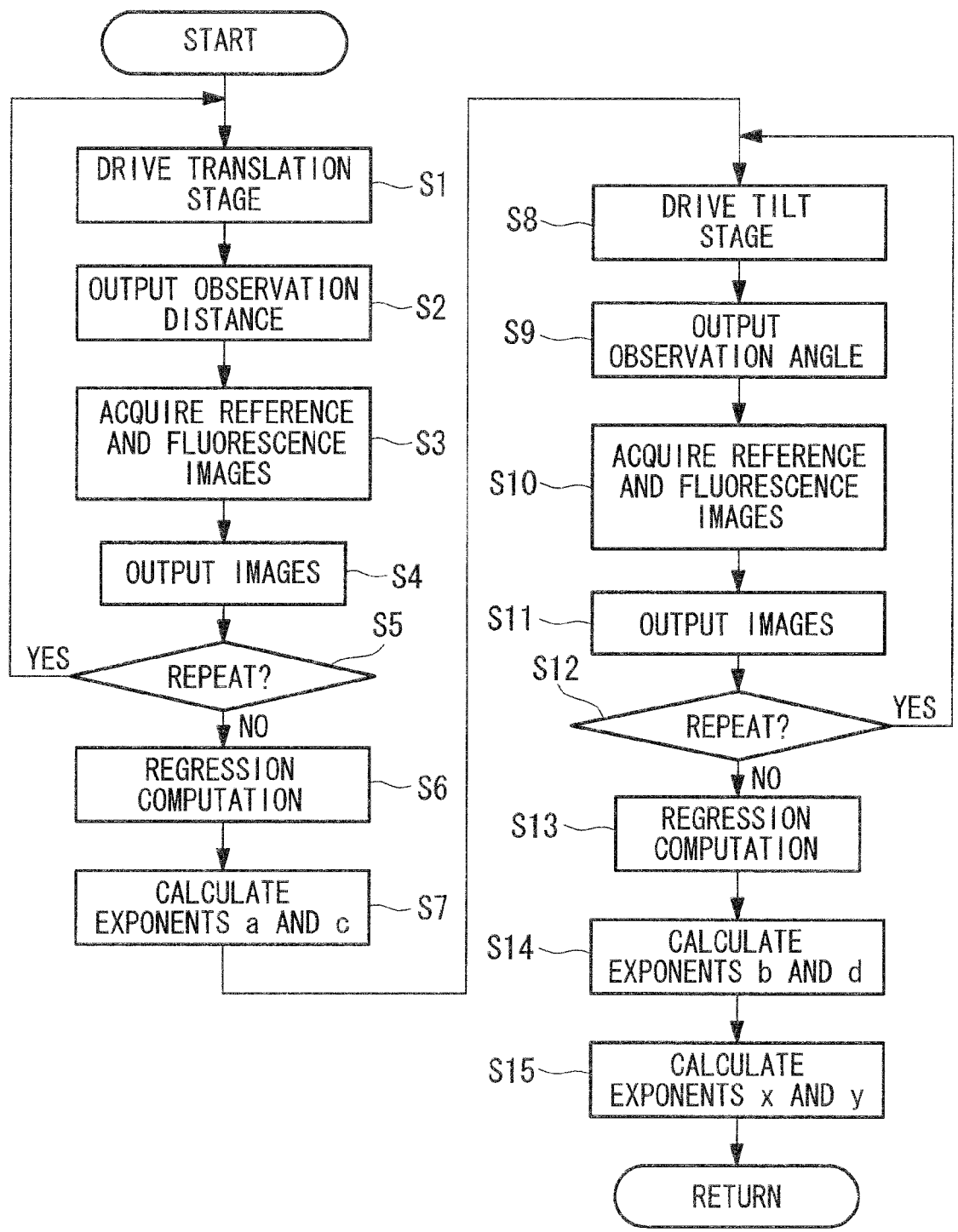
FIG. 11 is a flowchart for explaining processing in a controller in the fluoroscopy system in FIG. 9.

As shown in FIG. 11, the controller 47 first drives the translation stage 45 so that the end face 2a of the inserted portion 2 is at an observation starting distance from the surface of the standard specimen 44 (Step S1) and outputs the observation distance D at this time to the dependency-constant determining unit 42 of the fluoroscopy apparatus 1 (Step S2). In this state, the standard specimen 44 is irradiated with the illumination light and the excitation light from the illumination unit 4, and the return light and fluorescence are captured (Step S3). The luminance values of the fluorescence image $G_2$ generated at the fluorescence-image generating unit 21 and the luminance values of the reference image $G_1$ generated at the reference-image generating unit 20 are sent to the dependency-constant determining unit 42 (Step S4).

Then, the controller 47 repeats the above-described Steps S1 to S4 multiple times a predetermined number of times (Step S5). Accordingly, the standard specimen 44 is moved so that the distance between the end face 2a of the inserted portion 2 and the surface of the standard specimen 44 takes a plurality of observation distances D, and the observation distance D is output to the dependency-constant determining unit 42 each time. The luminance values of the florescence image $G_2$ and the luminance values of the reference image $G_1$ obtained at each observation distance D are sent from the fluorescence-image generating unit 21 and the reference-image generating unit 20 to the dependency-constant determining unit 42. Accordingly, at the dependency-constant determining unit 42, datasets of a plurality of observation distances D and the luminance values of the fluorescence images $G_2$ and the reference images $G_1$ associated therewith are stored, and, when the predetermined number of datasets are collected, power function regression is applied (Step S6), and the exponents a and c that indicate the dependency on the observation distance D are calculated (Step S7) as described above.

Next, the controller 47 drives the translation stage 45 and the tilt stage 46 so that the end face 2a of the inserted portion 2 is at the observation starting distance and angle relative to the surface of the standard specimen 44 (Step S8) and outputs the observation angle θ at this time to the dependency-constant determining unit 42 of the fluoroscopy apparatus 1 (Step S9). In this state, the standard specimen 44 is irradiated with the illumination light and the excitation light from the illumination unit 4, and the return light and fluorescence are imaged (Step S10). The luminance values of the fluorescence image $G_2$ generated at the fluorescence-image generating unit 21 and the luminance values of the reference image $G_1$ generated at the reference-image generating unit 20 are sent to the dependency-constant determining unit 42 (Step S11).

Then, the controller 47 repeats the above-described Steps S8 to S11 multiple times for a predetermined number of times (Step S12). Accordingly, the standard specimen 44 is moved so that the angle between the end face 2a of the inserted portion 2 and the surface of the standard specimen 44 takes a plurality of observation angles θ, and the observation angle θ is output to the dependency-constant determining unit 42 each time. The luminance values of florescence image $G_2$ and luminance values of reference image $G_1$ obtained at each observation angle θ are sent to the dependency-constant determining unit 42 from the fluorescence-image generating unit 21 and the reference-image generating unit 20. Accordingly, at the dependency-constant determining unit 42, datasets of a plurality of observation angles θ and the luminance values of the fluorescence images $G_2$ and the reference images $G_1$ associated therewith are stored, and, when the predetermined number of datasets are collected, power function regression is applied (Step S13), and the exponents b and d that indicate the dependency on the observation angle θ are calculated (Step S14) as described above. Then, by using the exponents a to d determined in this way and the constants m and n, which are set on the basis of the preset permissible error $e_{max}$, the exponents x and y for correcting the fluctuation in luminance value are calculated (Step S15).

In this way, with the fluoroscopy system 40 according to this embodiment, an advantage is afforded in that, even if the subject X or observation conditions, for example, the individual optical systems, fluorescence wavelength used for observation, etc., are changed, the exponents x and y for which the error rate is smaller than the maximum permissible error rate $e_{max}$ can be set, and observation can be performed with a fluorescence image $G_3$ having high quantitativeness even with various subjects X and observation conditions.

For example, when applied to an endoscope serving as the fluoroscopy apparatus 1, even if there are different types, such as a rigid scope and a flexible scope, or differences in observation sites, such as an endoscope for upper digestive organs and an endoscope for lower digestive organs, optimal correction exponents x and y can be set according to each one. Even for the same type of fluoroscopy apparatus 1, optimal exponents x and y can be set for individual apparatuses regardless of individual differences.

In this way, an advantage is afforded in that observation can be performed with a fluorescence image having high quantitativeness by satisfactorily removing dependencies on distance and angle remaining in an image that has been subjected to division.

As the standard specimen 44 in this embodiment, a phantom having the same scattering and absorption characteristics as a biological specimen to be observed may be used, or human or animal (pig, mouse, etc.) excised tissue may be used.

Here, an example experiment employing the fluoroscopy system 40 according to this embodiment will be described below with reference to the drawings.

Light in a band including white light and excitation light for a fluorescent agent (wavelength band of 400 to 740 nm) was used as the illumination light, and a reflected-light image of the illumination light reflected at and returning from a surface of a specimen Y was employed as the reference image $G_1$. A fluorescence image generated from a fluorochrome Cy7 injected into the specimen Y was employed as the fluorescence image $G_2$. A removed pig rectum was used as the specimen Y.

Figure 12A:
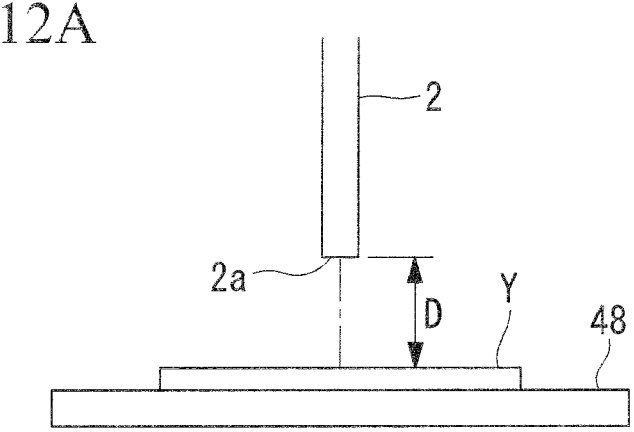
FIG. 12A is a diagram for explaining measurement of distance dependency in the fluoroscopy system in FIG. 9.
Figure 12B:
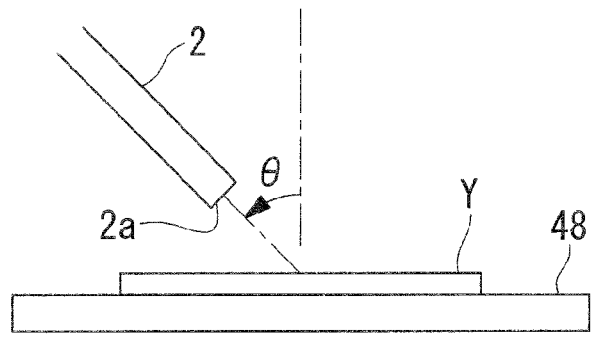
FIG. 12B is a diagram for explaining measurement of angular dependency in the fluoroscopy system in FIG. 9.

As shown in FIGS. 12A and 12B, the end face 2a of the inserted portion 2 was made to oppose the surface of the specimen Y.

Figure 13A:
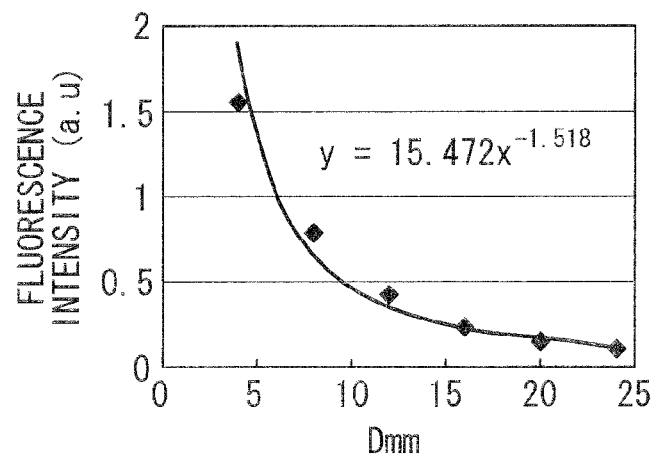
FIG. 13A is a diagram showing a graph of the observation distance characteristic based on the results of the measurement in FIG. 12A and a power approximation curve based thereon.
Figure 13B:
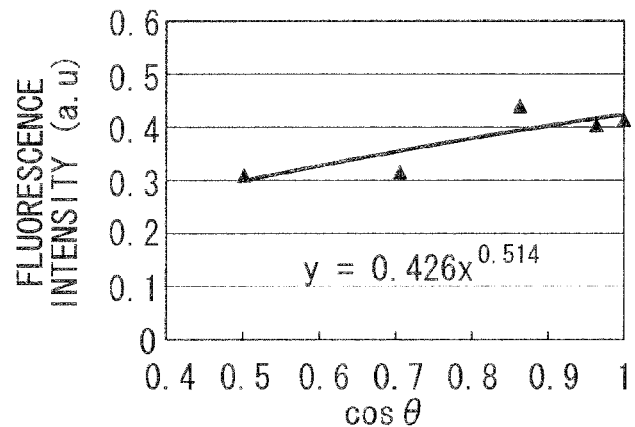
FIG. 13B is a diagram showing a graph of the observation angle characteristic based on the results of the measurement in FIG. 12B and a power approximation curve based thereon.
Figure 13C:
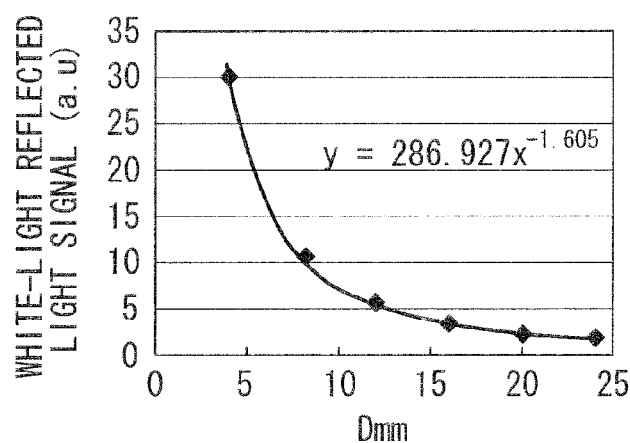
FIG. 13C is a diagram showing a graph of the observation distance characteristic based on the results of the measurement results in FIG. 12A and a power approximation curve based thereon.

For FIG. 12A, which is a measurement diagram for the distance dependency, the reference images $G_1$ and the fluorescence images $G_2$ were acquired by radiating the illumination light and the excitation light at a plurality of observation distances D while increasing the observation distances D by lowering the translation stage 45 at a position where an axial line of the inserted portion 2 was parallel to a normal of a mounting surface 48 of the translation stage 45. As a result, plots showing the observation distance characteristics, such as those shown in FIGS. 13A and 13C, were obtained.

Figure 13D:
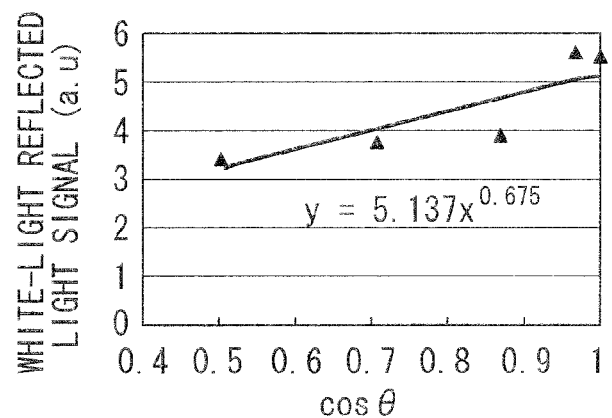
FIG. 13D is a diagram showing a graph of the observation angle characteristic based on the results of the measurement in FIG. 12B and a power approximation curve based thereon.

For FIG. 12B, which is a measurement diagram for the angular dependency, the reference images $G_1$ and the fluorescence images $G_2$ were acquired by radiating the illumination light and the excitation light at a plurality of observation angles while rotating around a center line disposed on the mounting surface 48 from the position where the axial line of the inserted portion 2 was parallel to the normal of the mounting surface 48. As a result, plots showing the observation angle characteristics, such as those shown in FIGS. 13B and 13D, were obtained.

Then, as shown with solid lines in the figures, when the exponents a and c related to the observation distance and the exponents b and d related to the observation angle were calculated by regression of these plots to a curve $Y = P \cdot X^Q$ (where X is on the horizontal axis, Y is on the vertical axis, P is a constant, and Q is an exponent), $a = -1.518$, $b = 0.514$, $c = -1.605$, and $d = 0.675$ were obtained.

REFERENCE SIGNS LIST

| X | subject |
|---|---|
| 1 | fluoroscopy apparatus |
| 2 | inserted portion (attachable/detachable part) |
| 3 | light source |
| 4 | illumination unit (illumination portion) |
| 6 | image-correcting unit |
| 17 | image-acquisition device (return-light imaging unit) |
| 18 | image-acquisition device (fluorescence imaging unit) |
| 32 | reading device (identification-information reading device) |
| 33 | storage unit |
| 40 | fluoroscopy system |
| 41 | calibration device |
| 32 | dependency-constant determining unit (exponent calculating unit) |
| 44 | standard specimen |
| 45 | translation stage (observation-state setting mechanism) |
| 46 | tilt stage (observation-state setting mechanism) |

The invention claimed is:

1. A fluoroscopy apparatus comprising:
an illumination portion provided with a light source that radiates illumination light and excitation light;
a fluorescence imaging unit that acquires a fluorescence image by imaging fluorescence generated at an subject;
a return-light imaging unit that acquires a reference image by imaging return light returning from the subject; and
an image-correcting unit that corrects the fluorescence image acquired by the fluorescence imaging unit by using the reference image imaged by the return-light imaging unit,
wherein the image-correcting unit performs the following processing:

$$FL_{revised} = FL_{after}/RL_{after},$$

where,
$FL_{revised}$ is a luminance value of the corrected fluorescence image,
$FL_{after} = A \times FL_{before}^x$,
$RL_{after} = B \times RL_{before}^y$,
$FL_{before}$ and $RL_{before}$ are luminance values of the acquired fluorescence image and reference image,
A and B are constants, $$x = (cn - dm)/(bc - ad), \quad \text{Expression (1):}$$

$$y = (an - bm)/(bc - ad), \quad \text{Expression (2):}$$

a is a value obtained by applying a power approximation to a characteristic of luminance versus distance from the illumination portion to the subject, for the fluorescence image obtained by the fluorescence imaging unit when excitation light of a predetermined intensity is radiated toward the subject,
b is a value obtained by applying a power approximation to a characteristic of luminance versus cosine from the illumination portion to the subject, for the fluorescence image obtained by the fluorescence imaging unit when excitation light of a predetermined intensity is radiated toward the subject,
c is a value obtained by applying a power approximation to a characteristic of luminance versus distance from the illumination portion to the subject, for the reference image obtained by the return-light imaging unit when illumination light of a predetermined intensity is radiated toward the subject,
d is a value obtained by applying a power approximation to a characteristic of luminance versus cosine from the illumination portion to the subject, for the reference image obtained by the return-light imaging unit when illumination light of a predetermined intensity is radiated toward the subject, $$r_D^{|m|} \cdot r_\theta^{|n|} \leq 1 + e_{max}, \quad \text{Expression (3):}$$

$r_D = D_{max}/D_{min}$,
$r_\theta = \cos\theta_{min}/\cos\theta_{max}$,
$D_{max}$ is a presumed maximum observation distance,
$D_{min}$ is a presumed minimum observation distance,
$\theta_{max}$ is a presumed maximum observation angle,
$\theta_{min}$ is a presumed minimum observation angle (where, $0° \leq \theta_{min} < \theta_{max} \leq 90°$),
m and n are arbitrary constants that satisfy Expression (3),
$e_{max}$ is $(FL_{after}/RL_{after})_{max} \div (FL_{after}/RL_{after})_{min} - 1$,
$(FL_{after}/RL_{after})_{max}$ is a maximum value within a range from the presumed minimum observation distance to the presumed maximum observation distance and within a range from the presumed minimum observation angle to the presumed maximum observation angle, and ($FL_{after}/RL_{after})_{min}$ is a minimum value within a range from the presumed minimum observation distance to the presumed maximum observation distance and within a range from the presumed minimum observation angle to the presumed maximum observation angle, and when bc−ad=0, x and y are set from arbitrary real numbers that satisfy x:y=c:a=d:b.

2. A fluoroscopy apparatus comprising:

an illumination portion provided with a light source that radiates illumination light and excitation light;

a fluorescence imaging unit that acquires a fluorescence image by imaging fluorescence generated at an subject;

a return-light imaging unit that acquires a reference image by imaging return light returning from the subject; and an image-correcting unit that corrects the fluorescence image acquired by the fluorescence imaging unit by using the reference image imaged by the return-light imaging unit, wherein the image-correcting unit performs the following processing:

$$FL_{revised} = (FL_{after}/RL_{after})^{1/x},$$

where $FL_{revised}$ is a luminance value of the corrected fluorescence image, $FL_{after} = A \times FL_{before}^{x}$, $RL_{after} = B \times RL_{before}^{y}$, $FL_{before}$ and $RL_{before}$ are luminance values of the acquired fluorescence image and reference image, A and B are constants, $$x:y=c:(a-m)=d:(b-n), \quad \text{Expression (4):}$$

a is a value obtained by applying a power approximation to a characteristic of luminance versus distance from the illumination portion to the subject, for the fluorescence image obtained by the fluorescence imaging unit when excitation light of a predetermined intensity is radiated toward the subject, b is a value obtained by applying a power approximation to a characteristic of luminance versus cosine from the illumination portion to the subject, for the fluorescence image obtained by the fluorescence imaging unit when excitation light of a predetermined intensity is radiated toward the subject, c is a value obtained by applying a power approximation to a characteristic of luminance versus distance from the illumination portion to the subject, for the reference image obtained by the return-light imaging unit when illumination light of a predetermined intensity is radiated toward the subject, d is a value obtained by applying a power approximation to a characteristic of luminance versus cosine from the illumination portion to the subject, for the reference image obtained by the return-light imaging unit when illumination light of a predetermined intensity is radiated toward the subject, $$r_D^{|m|} \cdot r_\theta^{|n|} \leq 1 + e_{max}, \quad \text{Expression (3):}$$

$r_D = D_{max}/D_{min}$, $r_\theta = \cos\theta_{min}/\cos\theta_{max}$, $D_{max}$ is a presumed maximum observation distance, $D_{min}$ is a presumed minimum observation distance, $\theta_{max}$ is a presumed maximum observation angle, $\theta_{min}$ is a presumed minimum observation angle (where, $0° \leq \theta_{min} < \theta_{max} \leq 90°$), m and n are arbitrary constants that satisfy Expression (4) and Expression (3), $e_{max}$ is $(FL_{after}/RL_{after})_{max} \div (FL_{after}/RL_{after})_{min} - 1$, $(FL_{after}/RL_{after})_{max}$ is a maximum value within a range from the presumed minimum observation distance to the presumed maximum observation distance and within a range from the presumed minimum observation angle to the presumed maximum observation angle, and $(FL_{after}/RL_{after})_{min}$ is a minimum value within a range from the presumed minimum observation distance to the presumed maximum observation distance and within a range from the presumed minimum observation angle to the presumed maximum observation angle.

3. A fluoroscopy apparatus according to claim 1, wherein the image-correcting unit additionally raises the luminance value $FL_{revised}$ of the corrected fluorescence image to the $1/x^{th}$ power.

4. A fluoroscopy apparatus according to claim 1, further comprising an attachable/detachable part that is detached/attached to change observation conditions, wherein the attachable/detachable part stores identification information, and wherein an identification-information reading device that reads the identification information stored in the attachable/detachable part and a storage unit that stores the identification information in association with the exponents x and y are provided.

5. A fluoroscopy apparatus according to claim 1 or 2, wherein m=0.

6. A fluoroscopy apparatus according to claim 2, wherein the illumination portion emits illumination light of a predetermined wavelength, the exponents x and y are set so as to substantially satisfy x:y=c:a or x:y=d:b, and the wavelength of the illumination light is set so that an absolute value of c becomes a minimum value assuming that ad−bc=ϵ.

7. A fluoroscopy apparatus according to claim 2, further comprising an attachable/detachable part that is detached/attached to change observation conditions, wherein the attachable/detachable part stores identification information, and wherein an identification-information reading device that reads the identification information stored in the attachable/detachable part and a storage unit that stores the identification information in association with the exponents x and y are provided.

8. A fluoroscopy system comprising:

a fluoroscopy apparatus according to claim 1 and a calibration device for calibrating the fluoroscopy apparatus, wherein the calibration device is provided with a standard specimen and an observation-state setting mechanism that changeably sets an observation distance and an observation angle of the fluoroscopy apparatus relative to the standard specimen, and one of the fluoroscopy apparatus and the calibration device is provided with an exponent calculating unit that calculates the above-described values a to d on the basis of the observation distance and the observation angle set with the observation-state setting mechanism and the fluorescence image and the reference image acquired by imaging the standard specimen.

9. A fluorescence-image processing method comprising:

irradiating a subject with excitation light from an illumination portion;

acquiring a fluorescence image by imaging fluorescence generated at the subject;

acquiring a reference image by imaging return light returning from the subject; and performing the following correction processing on the fluorescence image that corrects the fluorescence image by using the reference image acquired by imaging return light returning from the subject:

$$FL_{revised} = FL_{after}/RL_{after},$$

where, $FL_{revised}$ is a luminance value of the corrected fluorescence image, $FL_{after} = A \times FL_{before}^{x}$, $RL_{after} = B \times RL_{before}^{y}$, $FL_{before}$ and $RL_{before}$ are luminance values of the acquired fluorescence image and reference image, A and B are constants, $$x = (cn-dm)/(bc-ad), \quad \text{Expression (1):}$$

$$y = (an-bm)/(bc-ad), \quad \text{Expression (2):}$$

a is a value obtained by applying a power approximation to a characteristic of luminance versus distance from the illumination portion to the subject, for the fluorescence image obtained when excitation light of a predetermined intensity is radiated toward the subject, b is a value obtained by applying a power approximation to a characteristic of luminance versus cosine from the illumination portion to the subject, for the fluorescence image obtained when excitation light of a predetermined intensity is radiated toward the subject, c is a value obtained by applying a power approximation to a characteristic of luminance versus distance from the illumination portion to the subject, for the reference image obtained when illumination light of a predetermined intensity is radiated toward the subject, d is a value obtained by applying a power approximation to a characteristic of luminance versus cosine from the illumination portion to the subject, for the reference image obtained when illumination light of a predetermined intensity is radiated toward the subject, $$r_D^{|m|} \cdot r_\theta^{|n|} \leq 1 + e_{max}, \quad \text{Expression (3):}$$

$r_D = D_{max}/D_{min}$, $r_\theta = \cos\theta_{min}/\cos\theta_{max}$, $D_{max}$ is a presumed maximum observation distance, $D_{min}$ is a presumed minimum observation distance, $\theta_{max}$ is a presumed maximum observation angle, $\theta_{min}$ is a presumed minimum observation angle (where, $0° \leq \theta_{min} < \theta_{max} \leq 90°$), m and n are arbitrary constants that satisfy Expression (1), $e_{max}$ is $(FL_{after}/RL_{after})_{max} \div (FL_{after}/RL_{after})_{min} - 1$, $(FL_{after}/RL_{after})_{max}$ is a maximum value within a range from the presumed minimum observation distance to the presumed maximum observation distance and within a range from the presumed minimum observation angle to the presumed maximum observation angle, $(FL_{after}/RL_{after})_{min}$ is a minimum value within a range from the presumed minimum observation distance to the presumed maximum observation distance and within a range from the presumed minimum observation angle to the presumed maximum observation angle, and when $bc-ad=0$, x and y are set from arbitrary real numbers that satisfy $x:y=c:a=d:b$.

10. A fluorescence-image processing method comprising:
irradiating a subject with excitation light from an illumination portion;
acquiring a fluorescence image by imaging fluorescence generated at the subject;
acquiring a reference image by imaging return light returning from the subject; and
performing the following correction processing on the fluorescence image that corrects the fluorescence image by using the reference image acquired by imaging return light returning from the subject:

$$FL_{revised} = (FL_{after}/RL_{after})^{1/x},$$

where, $FL_{revised}$ is a luminance value of the corrected fluorescence image, $FL_{after} = A \times FL_{before}^{x}$, $RL_{after} = B \times RL_{before}^{y}$, $FL_{before}$ and $RL_{before}$ are luminance values of the acquired fluorescence image and reference image, A and B are constants, $$x:y = c:(a-m) = d:(b-n), \quad \text{Expression (4):}$$

a is a value obtained by applying a power approximation to a characteristic of luminance versus distance from the illumination portion to the subject, for the fluorescence image obtained by a fluorescence imaging unit when excitation light of a predetermined intensity is radiated toward the subject, b is a value obtained by applying a power approximation to a characteristic of luminance versus cosine from the illumination portion to the subject, for the fluorescence image obtained by the fluorescence imaging unit when excitation light of a predetermined intensity is radiated toward the subject, c is a value obtained by applying a power approximation to a characteristic of luminance versus distance from the illumination portion to the subject, for the reference image obtained by a return-light imaging unit when illumination light of a predetermined intensity is radiated toward the subject, d is a value obtained by applying a power approximation to a characteristic of luminance versus cosine from the illumination portion to the subject, for the reference image obtained by the return-light imaging unit when illumination light of a predetermined intensity is radiated toward the subject, $$r_D^{|m|} \cdot r_\theta^{|n|} \leq 1 + e_{max}, \quad \text{Expression (3):}$$

$r_D = D_{max}/D_{min}$, $r_\theta = \cos\theta_{min}/\cos\theta_{max}$, $D_{max}$ is a presumed maximum observation distance, $D_{min}$ is a presumed minimum observation distance, $\theta_{max}$ is a presumed maximum observation angle, $\theta_{min}$ is a presumed minimum observation angle (where, $0° \leq \theta_{min} < \theta_{max} < 90°$), m and n are arbitrary constants that satisfy Expression (4) and Expression (3), $e_{max}$ is $(FL_{after}/RL_{after})_{max} \div (FL_{after}/RL_{after})_{min} - 1$, $(FL_{after}/RL_{after})_{max}$ is a maximum value within a range from the presumed minimum observation distance to the presumed maximum observation distance and within a range from the presumed minimum observation angle to the presumed maximum observation angle, and $(FL_{after}/RL_{after})_{min}$ is a minimum value within a range from the presumed minimum observation distance to the presumed maximum observation distance and within a range from the presumed minimum observation angle to the presumed maximum observation angle.

11. A fluoroscopy system comprising:
a fluoroscopy apparatus according to claim 2 and
a calibration device for calibrating the fluoroscopy apparatus,
wherein the calibration device is provided with a standard specimen and an observation-state setting mechanism that changeably sets an observation distance and an observation angle of the fluoroscopy apparatus relative to the standard specimen, and
one of the fluoroscopy apparatus and the calibration device is provided with an exponent calculating unit that calculates the above-described values a to d on the basis of the observation distance and the observation angle set with the observation-state setting mechanism and the fluorescence image and the reference image acquired by imaging the standard specimen.

\* \* \* \* \*